(12) United States Patent
Vaingast et al.

(10) Patent No.: US 8,423,132 B2
(45) Date of Patent: Apr. 16, 2013

(54) EFFICIENT DYNAMIC STIMULATION IN AN IMPLANTED DEVICE

(75) Inventors: Shai Vaingast, Ganei-Tikva (IL); Ehud Cohen, Ganei-Tivka (IL)

(73) Assignee: Bio Control Medical (B.C.M.) Ltd., Yehud (IL)

( * ) Notice: Subject to any disclaimer, the term of this patent is extended or adjusted under 35 U.S.C. 154(b) by 1988 days.

(21) Appl. No.: 10/538,521

(22) PCT Filed: Dec. 11, 2003

(86) PCT No.: PCT/IL03/01062
§ 371 (c)(1),
(2), (4) Date: Jan. 11, 2006

(87) PCT Pub. No.: WO2004/052444
PCT Pub. Date: Jun. 24, 2004

(65) Prior Publication Data
US 2006/0265027 A1    Nov. 23, 2006

Related U.S. Application Data

(60) Provisional application No. 60/432,932, filed on Dec. 12, 2002.

(51) Int. Cl.
*A61N 1/00* (2006.01)
(52) U.S. Cl.
USPC .................................................. 607/2; 607/8
(58) Field of Classification Search ............... 607/28, 607/52, 2, 8
See application file for complete search history.

(56) References Cited

U.S. PATENT DOCUMENTS

| | | | |
|---|---|---|---|
| 3,628,538 A | 12/1971 | Vincent et al. | |
| 3,662,758 A | 5/1972 | Glover | |
| 4,222,385 A * | 9/1980 | Backhouse | 607/9 |
| 4,543,956 A * | 10/1985 | Herscovici | 607/13 |
| 5,103,835 A | 4/1992 | Yamada et al. | |
| 5,144,948 A | 9/1992 | Anderson et al. | |
| 5,186,170 A | 2/1993 | Varrichio et al. | |
| 5,201,865 A * | 4/1993 | Kuehn | 607/8 |
| 5,233,982 A | 8/1993 | Kohl | |
| 5,235,980 A | 8/1993 | Varrichio et al. | |
| 5,300,093 A | 4/1994 | Koestner et al. | |
| 5,314,458 A * | 5/1994 | Najafi et al. | 607/116 |
| 5,391,191 A | 2/1995 | Holmstrom | |
| 5,411,548 A | 5/1995 | Carman et al. | |
| 5,431,686 A * | 7/1995 | Kroll et al. | 607/7 |
| 5,486,201 A * | 1/1996 | Canfield | 607/13 |
| 5,531,772 A | 7/1996 | Prutchi | |
| 5,562,717 A | 10/1996 | Tippey et al. | |
| 5,722,997 A * | 3/1998 | Nedungadi et al. | 607/28 |
| 5,735,880 A | 4/1998 | Prutchi et al. | |

(Continued)

OTHER PUBLICATIONS

U.S. Appl. No. 60/432,932, filed Dec. 12, 2002, Vaingast, et al.

(Continued)

*Primary Examiner* — Joseph Stoklosa
(74) *Attorney, Agent, or Firm* — Sughrue Mion, PLLC

(57) ABSTRACT

A method for measuring impedance of a tissue (20), consisting of charging a capacitor (C15) to a potential, and discharging the capacitor for a discharge period through the tissue. The method further consists of measuring a voltage drop on the capacitor over the discharge period and determining the impedance of the tissue responsive to the potential, the voltage drop, and the discharge period.

16 Claims, 13 Drawing Sheets

U.S. PATENT DOCUMENTS 5,807,397 A      9/1998   Barreras et al.
5,843,136 A     12/1998   Zhu et al.
7,359,751 B1 *   4/2008   Erickson et al. ................ 607/27
7,450,987 B2 * 11/2008   Varrichio et al. ................ 607/2

OTHER PUBLICATIONS

European search report dated Aug. 10, 2006, which was issued during the prosecution of Applicant's European Patent Application No. EP 06 01 1641.

International Search Report issued by the International Searching Authority issued Nov. 18, 2004 in connection with related International Application No. PCT/IL2003/001062.

Van den Honert C et al., "A Technique for Collision Block of Peripheral Nerve: Frequency Dependence," MP-12, IEEE Trans. BME-28:379-382, May 1981.

An Examination Report, dated Jul. 13, 2011 which issued during the prosecution of EP Patent Application No. 03780564.5.

* cited by examiner

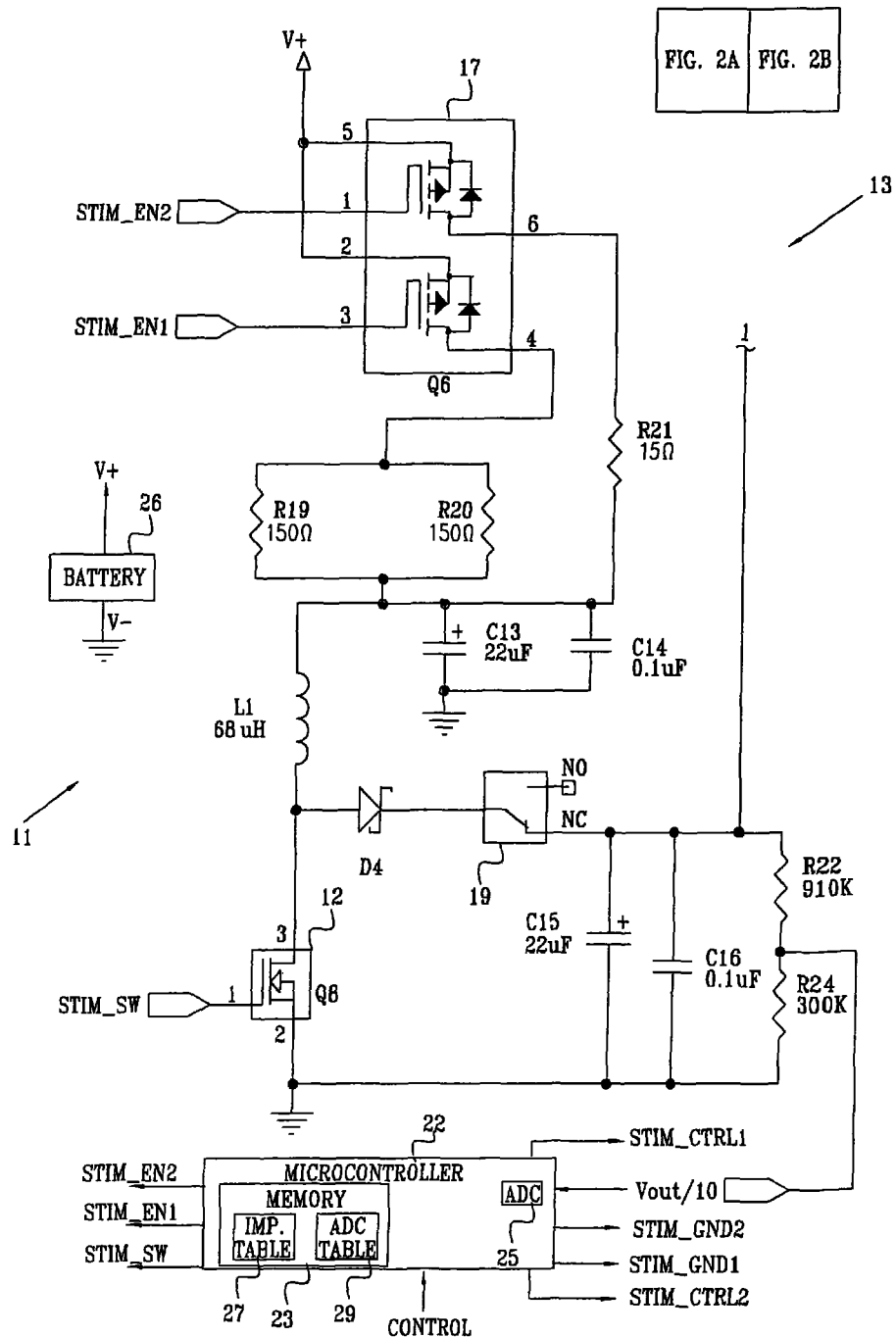

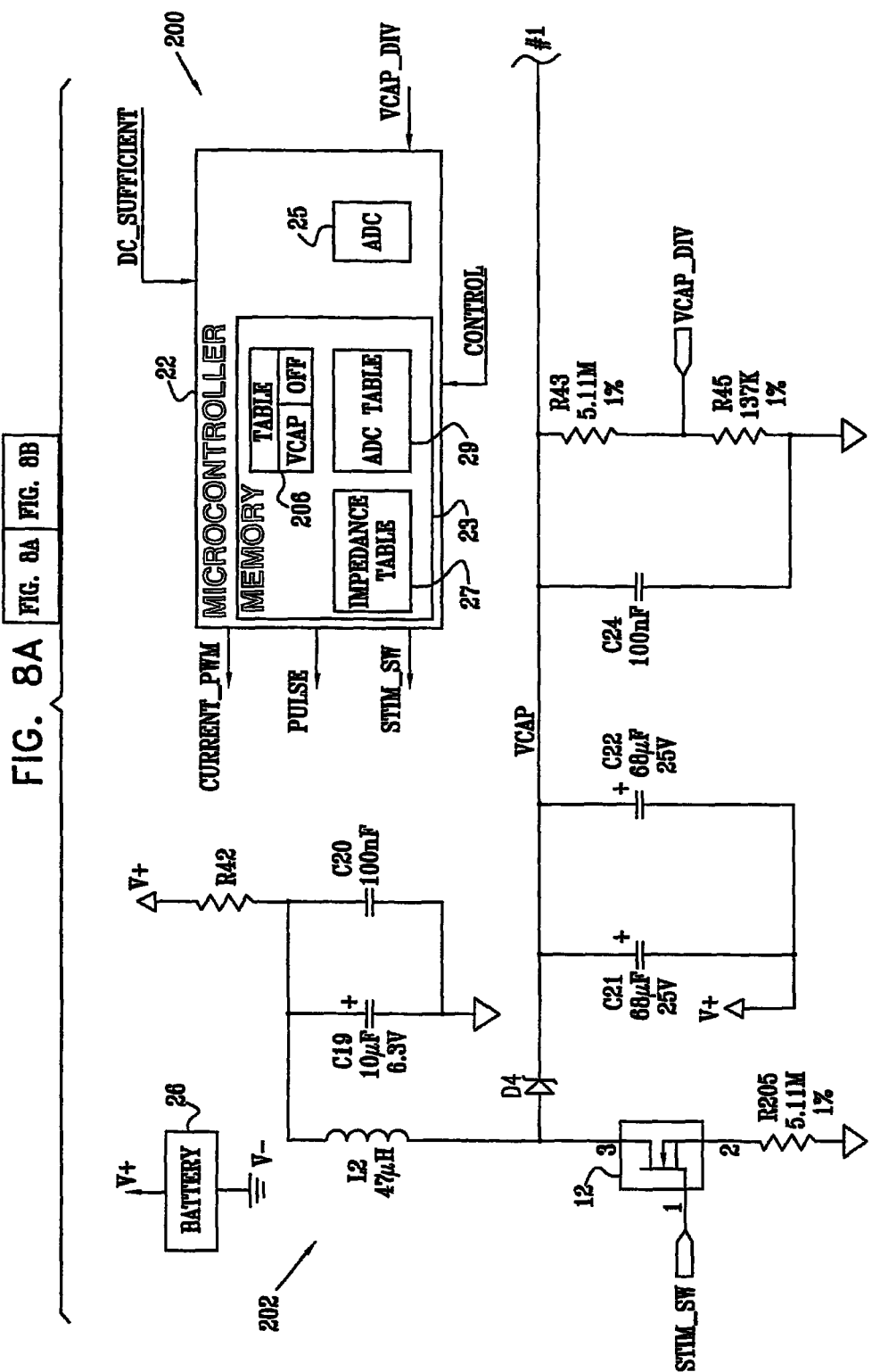

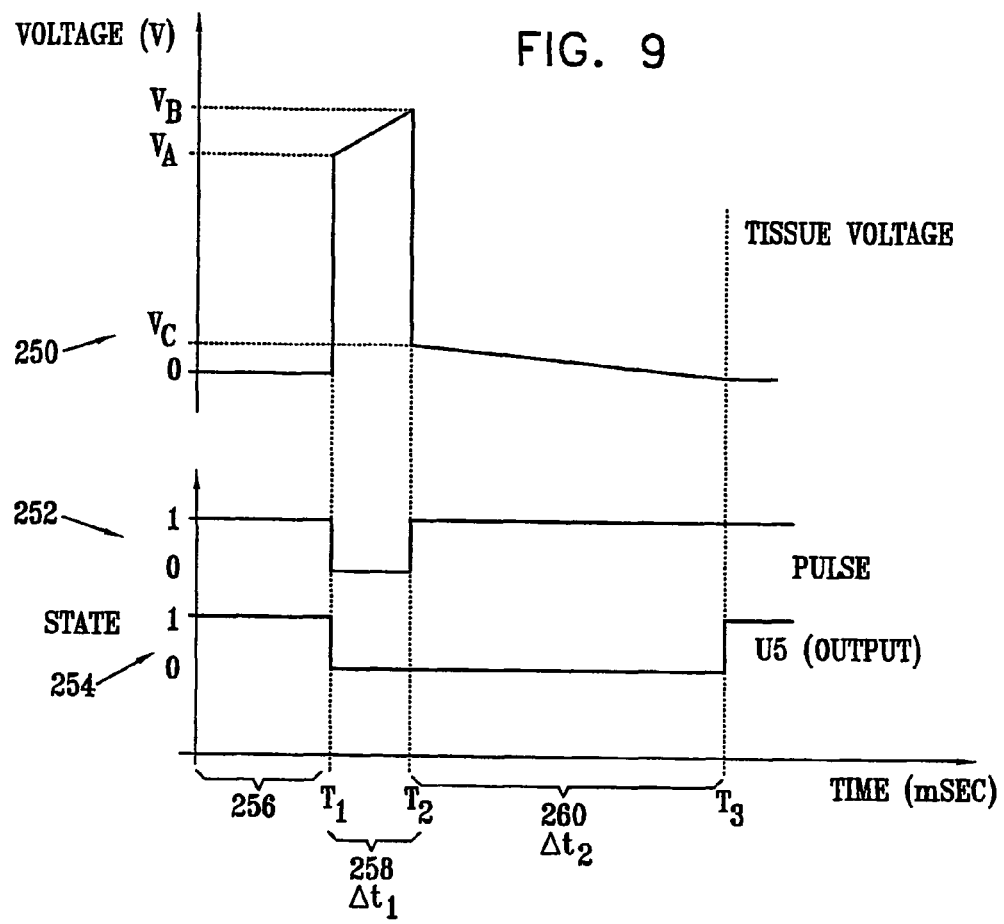
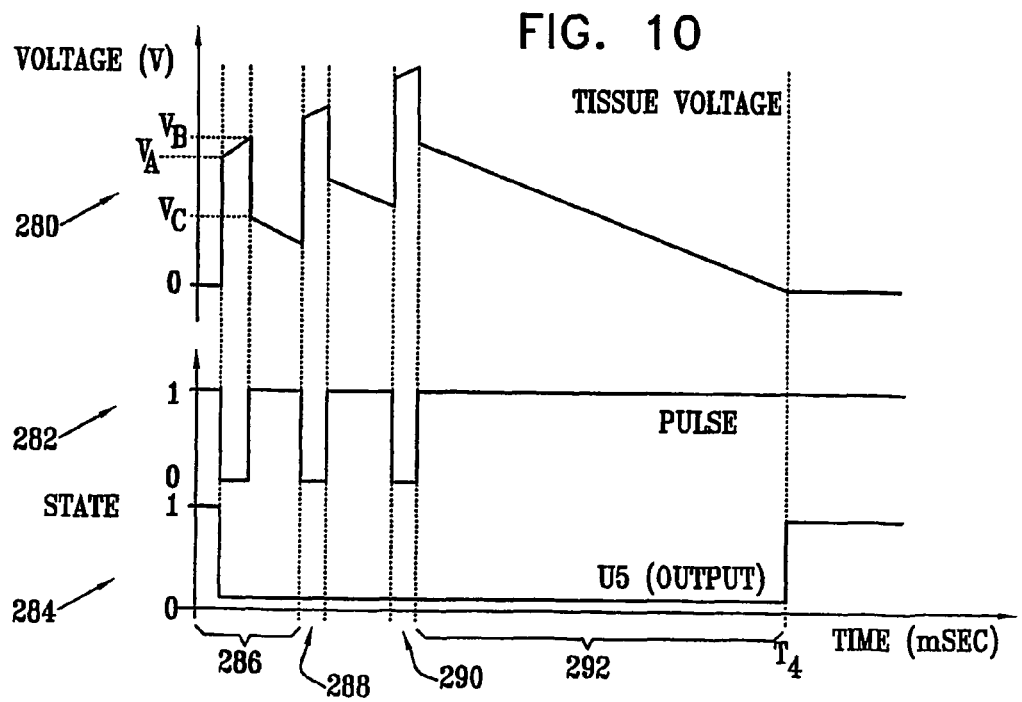

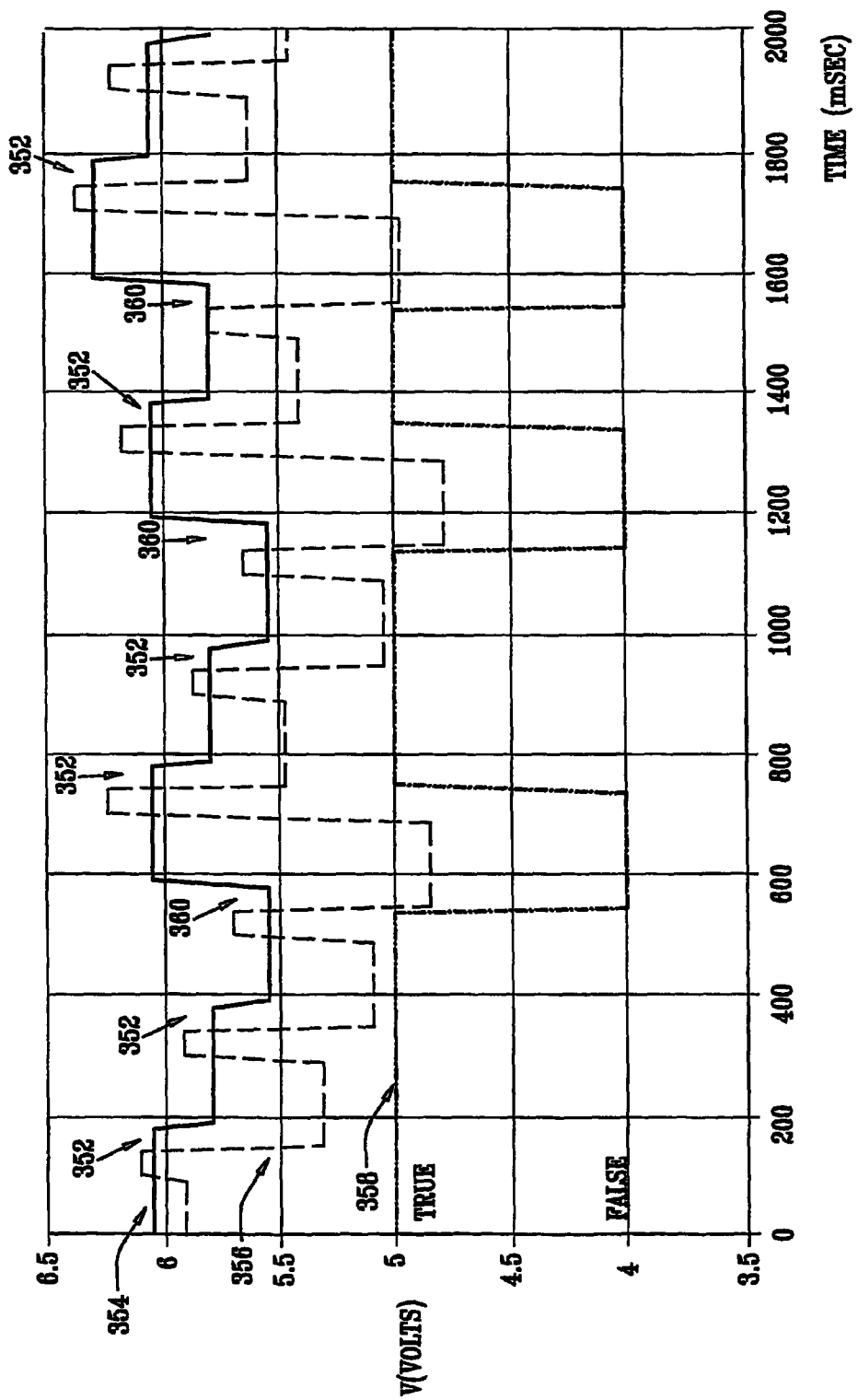

EFFICIENT DYNAMIC STIMULATION IN AN IMPLANTED DEVICE

CROSS-REFERENCE TO RELATED APPLICATION

This application is a §371 national stage of PCT International Application No. PCT/IL2003/001062, filed Dec. 11, 2003, claiming priority of U.S. Provisional Application No. 60/432,932, filed Dec. 12, 2002, the contents of all of which are hereby incorporated by reference.

FIELD OF THE INVENTION

The present invention relates generally to electrical pulse generators, and specifically to pulse generators for electrical stimulation of tissue.

BACKGROUND OF THE INVENTION

Stimulation of tissue of a subject by applying an electrical potential to the tissue is well known in the medical art. Herein, in the specification and in the claims, tissue is to be understood as comprising muscle and/or nerve of a subject. Levels and type of stimulation used depend on a number of factors, such as whether the stimulation is applied externally, and the desired effect of the stimulation. When the tissue is stimulated directly, by one or more electrodes implanted in the tissue, levels of stimulation needed to achieve a specific desired effect are typically orders of magnitude less than the levels needed if the tissue is stimulated externally and/or indirectly. Devices for direct tissue stimulation, such as cardiac pacemakers, are typically implanted into the subject, and typically rely on an internal battery for producing their pulses.

Different types of pulses are known in the art for producing muscle stimulation. In the specification and in the claims, a biphasic pulse is assumed to be a pair of pulses having alternating positive and negative potentials, the biphasic pulse being able to stimulate the tissue; a mono-phase pulse is assumed to be a single uni-directional pulse which is able to stimulate the tissue; and alternating pulses are assumed to comprise a sequence of mono-phase pulses having alternating positive and negative potentials, each mono-phase pulse being able to stimulate the tissue. Typically, a time period between the pair of pulses comprising a biphasic pulse is of the order of 500 µs; a time period between sequential alternating pulses is of the order of 25 ms.

U.S. Pat. No. 5,391,191, to Holmstrom, whose disclosure is incorporated herein by reference, describes an implanted device for tissue stimulation. The device incorporates a current sensing mechanism which is applied to reduce tissue polarization, electrolysis effects, and detect tissue reaction. The device is implemented to deliver biphasic pulses, as well as a mono-phase pulses. Both types of pulses are used for stimulation; to reduce energy consumption, the device implements the mono-phase pulses.

It will be appreciated that efficiency in battery utilization in implanted devices is an important consideration, in order to increase battery life before recharging and/or replacement of the battery is required.

Anodal break excitation, also known as anode break excitation, may occur at an anode if tissue stimulation is abruptly halted. Such excitation is typically an undesired side effect of the tissue stimulation, and methods to reduce or eliminate the effect have been sought.

SUMMARY OF THE INVENTION

It is an object of some aspects of the present invention to provide a method and apparatus for stimulating tissue of a subject.

It is a further object of some aspects of the present invention to reduce or eliminate anodal break excitation.

In a preferred embodiment of the present invention, a stimulation device comprises charging circuitry for charging a stimulation capacitor to an operating voltage level. Switching circuitry in the device is coupled to the charging circuitry. The switching circuitry generates both biphasic and alternating pulses, herein termed stimulation pulses, from uni-directional pulses which are generated by discharging the stimulation capacitor from the operating voltage level for a pulse period. The stimulation pulses are delivered to tissue of a subject by electrodes implanted therein, generating a tissue stimulation level which is a function of the operating voltage and the pulse period. Initially both the operating voltage and the pulse period are preset by an operator of the device, so as to achieve a desired tissue stimulation level. During operation of the device, a potential is measured on the stimulation capacitor at discharge, so as to measure an impedance of the tissue. Responsive to the impedance, the operating voltage level and/or the preset pulse period are adjusted in order to maintain the tissue stimulation level at the desired tissue stimulation level.

The charging circuitry is most preferably driven by an internal battery contained in the device. The charging circuitry, operated by a micro-controller, comprises a direct current (DC) charging circuit and an alternating current (AC) charging circuit which are each able to charge the stimulation capacitor by respective differential potentials. The micro-controller is able to minimize battery energy dissipation by using either or both circuits, and to set the time of use of each circuit in order to charge the stimulation capacitor to the initial operating voltage level. The AC circuit enables the operating voltage to be reached regardless of a voltage delivered by the battery. Similarly, for any adjusted operating voltage or other pulse parameter such as the pulse period, the micro-controller sets the time of use of each circuit so as to charge the stimulation capacitor to the adjusted operating voltage efficiently.

Parameters such as tissue impedance and operating voltage level are derived from measured potentials on the stimulation capacitor as it discharges. Thus, no current sensing mechanism, as is used by other tissue stimulators known in the art, is required in preferred embodiments of the present invention. Current sensing mechanisms, typically resistors, drain energy. Not implementing such a mechanism achieves a significant saving in energy supplied by a battery powering the stimulation device.

In some preferred embodiments of the present invention, a resistive element having a controlled resistance is coupled between the electrodes so as to be able to short-circuit an interface capacitance formed in the tissue being stimulated. The resistive element preferably comprises a field effect transistor (FET) having a gate which acts as a control electrode for the resistive element, the gate being activated by a control signal from the micro-controller. By short-circuiting the electrodes and the interface capacitance at times chosen by the micro-controller, electrolysis effects at the electrodes may be reduced and even eliminated, and the tissue stimulation level may be more precisely defined.

In preferred embodiments of the present invention, the micro-controller comprises an analog-to-digital converter (ADC). Most preferably, the stimulation device comprises a calibration circuit which generates a DC reference voltage which is substantially invariant even with variation of battery voltage from a battery powering the device. A memory in the micro-controller comprises a look-up table which has a one-to-one mapping between a digital value generated by the ADC responsive to the reference voltage and the battery voltage at which the ADC is operating. The look-up table also comprises a one-to-one mapping between the digital value and a multiplicative correction factor. The micro-controller multiplies other digital values, generated as the ADC is measuring voltages within the stimulation device, in order to adjust the other digital values due to changes in the battery voltage.

In an alternative preferred embodiment of the present invention, the charging circuitry is coupled to current controlled stimulation circuitry, rather than to the switching circuitry. The current controlled stimulation circuitry is configured to apply a pre-determined voltage-time relationship to the tissue. The voltage-time relationship is preferably substantially linear, and is applied to discharge the interface capacitance of the tissue being stimulated. By discharging the interface capacitance in a linear manner with a current limiter, anodal break excitation of the tissue is substantially eliminated.

There is therefore provided, according to a preferred embodiment of the present invention, a method for measuring impedance of a tissue, including:

charging a capacitor to a potential;

discharging the capacitor for a discharge period through the tissue;

measuring a voltage drop on the capacitor over the discharge period; and determining the impedance of the tissue responsive to the potential, the voltage drop, and the discharge period.

Preferably, charging the capacitor includes:

providing a first circuit which is adapted to charge the capacitor to a first voltage;

providing a second circuit which is adapted to charge the capacitor to a second voltage;

measuring the potential on the capacitor;

determining a first charging period for the first circuit and a second charging period for the second circuit, responsive to the potential, so that the first and second charging periods substantially total to the predetermined period and so that the first and second voltages substantially total to the predetermined differential potential; and operating the first circuit for the first charging period and the second circuit for the second charging period, the circuits being operated sequentially.

The first circuit preferably includes a resistive element through which the capacitor is charged by a substantially direct current (DC), and the second circuit preferably includes an inductor, a switching element, and a diode, which are operative to generate a substantially alternating current (AC) and to rectify the AC so as to charge the capacitor.

There is further provided, according to a preferred embodiment of the present invention, a method for stimulating a tissue, including:

charging a capacitor to a first potential;

discharging the capacitor for a first discharge period through the tissue;

measuring a voltage drop on the capacitor over the first discharge period;

determining an impedance of the tissue responsive to the first potential, the voltage drop, and the first discharge period;

determining a second potential and a second discharge period, responsive to the impedance and a predetermined desired tissue stimulation level;

charging the capacitor to the second potential; and discharging the capacitor for the second discharge period through the tissue.

Preferably, discharging the capacitor for the first discharge period and discharging the capacitor for the second discharge period each include discharging alternating pulses through the tissue, each alternating pulse including a positive-going pulse followed by a negative-going pulse, so that a time between the positive-going pulse and the negative-going pulse is substantially equal to half a period of the alternating pulses.

Discharging the capacitor for the first discharge period and discharging the capacitor for the second discharge period each preferably include discharging biphasic pulses through the tissue, each biphasic pulse including a positive-going pulse followed by a negative-going pulse, so that a time between the positive-going pulse and the negative-going pulse is substantially less than half a period of the biphasic pulses.

Further preferably, discharging the biphasic pulses includes discharging a first biphasic pulse including a first positive-going pulse followed by a first negative-going pulse, followed by a second biphasic pulse including a second negative-going pulse followed by a second positive-going pulse.

Preferably, discharging the capacitor for the first discharge period and discharging the capacitor for the second discharge period each include discharging the capacitor responsive to a control signal generated by the tissue.

The second discharge period is preferably subsequent to the first discharge period.

There is further provided, according to a preferred embodiment of the present invention, apparatus for measuring impedance of a tissue, including:

a capacitor; and circuitry which is adapted to:

charge the capacitor to a potential, discharge the capacitor for a discharge period through the tissue, measure a voltage drop on the capacitor over the discharge period, and determine the impedance of the tissue responsive to the potential, the voltage drop, and the discharge period.

Preferably, the circuitry includes:

a first circuit which is adapted to charge the capacitor to a first voltage;

a second circuit which is adapted to charge the capacitor to a second voltage;

and wherein the circuitry is further adapted to measure the potential on the capacitor, determine a first charging period for the first circuit and a second charging period for the second circuit, responsive to the potential, so that the first and second charging periods substantially total to the predetermined period and so that the first and second voltages substantially total to the predetermined differential potential, and operate the first circuit for the first charging period and the second circuit for the second charging period, the circuits being operated sequentially.

The first circuit preferably includes a resistive element through which the capacitor is charged by a substantially direct current (DC), and the second circuit preferably includes an inductor, a switching element, and a diode, which are operative to generate a substantially alternating current (AC) and to rectify the AC so as to charge the capacitor.

There is further provided, according to a preferred embodiment of the present invention, apparatus for changing a potential across a capacitor by a predetermined differential potential in a predetermined time period, including:

a first circuit which is adapted to charge the capacitor to a first voltage;

a second circuit which is adapted to charge the capacitor to a second voltage; and a controller which measures the potential on the capacitor, and responsive thereto and to the predetermined differential potential and the predetermined time period operates the first circuit and the second circuit sequentially for respective periods of time substantially totaling the predetermined time period so as to charge the capacitor by the predetermined differential potential substantially totaling the first and the second voltages.

The apparatus preferably includes a memory wherein is stored a first charging rate for the first circuit and a second charging rate for the second circuit, and wherein the controller is adapted to determine the respective periods of time responsive to the first and the second charging rates.

Preferably, the first circuit dissipates a first energy to charge the capacitor to the first voltage and the second circuit dissipates a second energy to charge the capacitor to the second voltage, and the controller is adapted to determine the respective periods of time responsive to the first and the second energies.

The controller is preferably adapted to determine the respective periods so that a sum of the first and the second energies is a minimum.

Preferably, the first circuit includes a resistive element through which the capacitor is charged by a substantially direct current (DC), and the second circuit includes an inductor, a switching element, and a diode, which are operative to generate a substantially alternating current (AC) and to rectify the AC so as to charge the capacitor.

The apparatus preferably includes a battery supplying a battery voltage, wherein the first circuit includes a resistive element through which the capacitor is charged by a substantially direct current (DC), and wherein the second circuit includes an inductor, a switching element, and a diode, which are operative to generate a substantially alternating current (AC) and to rectify the AC so as to charge the capacitor, wherein the first voltage is a predetermined fraction, greater than 0 and less than 1, of the battery voltage, and wherein the predetermined differential potential is greater than the battery voltage.

There is further provided, according to a preferred embodiment of the present invention, apparatus for stimulating a tissue having a tissue capacitance, including:

a capacitor;

circuitry which is adapted to:

charge the capacitor to a potential, discharge the capacitor for a discharge period through the tissue; and a resistive element, having a resistance which is controlled by the circuitry, and which is coupled to the circuitry and which is adapted to substantially short-circuit the tissue capacitance responsive to a control signal generated by the circuitry.

Preferably, the circuitry is adapted to generate the control signal at a time so as to implement a predetermined stimulation level to the tissue, and the time preferably directly follows a completion of the discharge period.

Preferably, the resistance includes a value so that substantially no anodal break excitation occurs in the tissue.

There is further provided, according to a preferred embodiment of the present invention, apparatus for measuring a voltage, including:

a battery which supplies a direct current (DC) voltage;

a DC voltage reference source, which generates a substantially invariant reference voltage, and which is powered by the battery;

an analog-to-digital converter (ADC) which generates a digital value responsive to receiving the reference voltage as an analog input, and which is powered by the battery;

a memory, comprising an ADC look-up table having a one-to-one mapping between the digital value and the DC voltage; and a processor, which is adapted to use the ADC look-up table to determine the DC voltage responsive to the digital value.

Preferably, the ADC look-up table includes a further one-to-one mapping between the digital value and a multiplicative correction factor which is operative to multiply the digital value so as to generate an improved digital value, and the ADC is adapted to receive an alternative DC voltage and to generate an alternative digital value responsive thereto, and the processor is adapted to determine the alternative DC voltage responsive to the alternative digital value and the multiplicative correction factor.

The apparatus preferably includes a plurality of resistors acting as a voltage divider which generate the alternative DC voltage, and one of the resistors preferably includes an internal resistance of the ADC.

There is further provided, according to a preferred embodiment of the present invention, a method for changing a potential across a capacitor by a predetermined differential potential in a predetermined time period, including:

providing a first circuit which is adapted to charge the capacitor to a first voltage;

providing a second circuit which is adapted to charge the capacitor to a second voltage;

measuring a potential on the capacitor;

determining a first charging period for the first circuit and a second charging period for the second circuit, responsive to the potential, so that the first and second charging periods substantially total to the predetermined period and so that the first and second voltages substantially total to the predetermined differential potential; and operating the first circuit for the first charging period and the second circuit for the second charging period, the circuits being operated sequentially.

The method preferably includes storing a first charging rate for the first circuit and a second charging rate for the second circuit in a memory, wherein determining the first charging period and the second charging period includes determining the charging periods responsive to the first and the second charging rates.

Preferably, the first circuit dissipates a first energy to charge the capacitor to the first voltage and the second circuit dissipates a second energy to charge the capacitor to the second voltage, and wherein determining the first charging period and the second charging period includes determining the charging periods responsive to the first and the second energies.

Preferably, determining the charging periods includes determining the charging periods so that a sum of the first and the second energies is a minimum.

Further preferably, the first circuit includes a resistive element through which the capacitor is charged by a substantially direct current (DC), and the second circuit includes an inductor, a switching element, and a diode, which are operative to generate a substantially alternating current (AC) and to rectify the AC so as to charge the capacitor.

The method preferably includes providing a battery that supplies a battery voltage, wherein the first circuit includes a resistive element through which the capacitor is charged by a substantially direct current (DC), and wherein the second circuit includes an inductor, a switching element, and a diode, which are operative to generate a substantially alternating current (AC) and to rectify the AC so as to charge the capacitor, wherein the first voltage is a predetermined fraction, greater than 0 and less than 1, of the battery voltage, and wherein the predetermined differential potential is greater than the battery voltage.

There is further provided, according to a preferred embodiment of the present invention, apparatus for stimulating tissue having a capacitance, including:

charge circuitry which is adapted to apply a potential to the tissue, causing a voltage to develop across the capacitance of the tissue; and discharge circuitry which is adapted to inject a current to the tissue so as to discharge the capacitance, the current being substantially independent of the voltage across the capacitance.

Preferably, the charge circuitry includes a stimulation capacitor, an inductor, and a micro-controller which is adapted to apply pulses having a variable duty cycle to the inductor, and wherein the micro-controller causes the inductor to charge the stimulation capacitor to the voltage by altering the variable duty cycle.

Preferably, the current is substantially fixed.

Preferably, the potential causes a stimulation current in the tissue, and the current injected by the discharge circuitry is preferably a substantially pre-set fraction of the stimulation current.

The current preferably includes a value that substantially eliminates anodal break excitation of the tissue, the value is preferably less than a pre-set fraction of a stimulation current caused by the potential, and the pre-set fraction is preferably approximately 5%.

The discharge circuitry is preferably adapted to measure the voltage across the capacitance, and is preferably adapted to halt injection of the current to the tissue when the voltage is substantially zero.

The apparatus preferably includes:

a battery having a first battery terminal and a second battery terminal coupled to ground and generating a battery voltage which powers at least a first part of the charge circuitry and at least a second part of the discharge circuitry; and a first and a second stimulation electrode between which the capacitance is formed, wherein the first battery terminal and the first stimulation electrode are connected, and wherein the charge circuitry generates the potential between the first and the second stimulation electrodes, and wherein the discharge circuitry injects the current between the first and the second stimulation electrodes.

The apparatus preferably also includes:

a stimulation capacitor which receives a stimulation potential generated by the charge circuitry; and a detector which monitors a second-stimulation-electrode potential on the second stimulation electrode, the detector being coupled between ground and the stimulation potential.

Further preferably, the apparatus includes a micro-controller which receives a Boolean signal from the detector in response to the second-stimulation-electrode potential, and which decrements a targeted voltage set by the micro-controller in response to the signal being true, and which increments the targeted voltage in response to the signal being false.

The apparatus preferably includes a micro-controller which is adapted to measure a time to discharge the capacitance, and to generate a measure of the capacitance in response to the time.

The apparatus preferably includes a micro-controller which is adapted to measure a time to apply the potential to the tissue, and to generate a measure of the capacitance in response to the time.

The apparatus preferably further includes:

a detector which monitors a state of at least part of the charge circuitry, and which generates a state signal in response to the state; and a micro-controller which receives the state signal and which sets the potential in response thereto.

Preferably, the micro-controller generates a pulse, at the potential, in a sequence of pulses and sets a target voltage in response to the state signal and the potential, and wherein the charge circuitry is adapted to alter the potential to a future potential in response to the target voltage, and to apply the future potential to a subsequent pulse in the sequence.

Further preferably, the charge circuitry is adapted to measure an impedance of the tissue, and to alter the potential applied to the tissue in response to the impedance.

There is further provided, according to a preferred embodiment of the present invention, a method for stimulating tissue having a capacitance, including:

applying a potential to the tissue so as to cause a voltage to develop across the capacitance of the tissue; and injecting a current to the tissue so as to discharge the capacitance, the current being substantially independent of the voltage across the capacitance.

Preferably, the current is substantially fixed.

Preferably, the potential causes a stimulation current in the tissue, and the current injected is a substantially pre-set fraction of the stimulation current, and the current preferably includes a value that substantially eliminates anodal break excitation of the tissue, and the value is preferably less than a pre-set fraction of a stimulation current caused by the potential, and the pre-set fraction is preferably approximately 5%.

The method preferably includes measuring the voltage across the capacitance, and halting injection of the current to the tissue when the voltage is substantially zero.

The method preferably includes:

providing a battery having a first battery terminal and a second battery terminal coupled to ground;

providing a first and a second stimulation electrode between which the capacitance is formed;

connecting the first battery terminal and the first stimulation electrode;

generating the potential between the first and the second stimulation electrodes;

injecting the current between the first and the second stimulation electrodes;

providing a stimulation capacitor which receives a stimulation potential in response to applying the potential;

coupling a detector between ground and the stimulation potential; and monitoring with the detector a second-stimulation-electrode potential on the second stimulation electrode.

The method preferably includes:

receiving a Boolean signal from the detector in response to the second-stimulation-electrode potential;

setting a targeted voltage;

decrementing the targeted voltage in response to the signal being true; and incrementing the targeted voltage in response to the signal being false.

The method preferably includes measuring a time to discharge the capacitance, and generating a measure of the capacitance in response to the time.

The method preferably includes measuring a time to apply the potential to the tissue, and generating a measure of the capacitance in response to the time.

The method preferably includes:

monitoring a state of charge circuitry adapted to apply the potential, and generating a state signal in response to the state; and receiving the state signal and setting the potential in response thereto.

The method preferably includes:

generating a pulse, at the potential, in a sequence of pulses and setting a target voltage in response to the state signal and the potential;

altering the potential to a future potential in response to the target voltage; and applying the future potential to a subsequent pulse in the sequence.

The method preferably includes measuring an impedance of the tissue, and altering the potential applied to the tissue in response to the impedance.

There is further provided, according to a preferred embodiment of the present invention, apparatus for stimulating tissue having a capacitance, including:

charge circuitry which is adapted to apply a potential to the tissue, causing a voltage to develop across the capacitance of the tissue;

discharge circuitry which is adapted to inject a current to the tissue so as to discharge the capacitance; and feedback circuitry which is adapted to monitor the potential and to control the current in response to the potential.

There is further provided, according to a preferred embodiment of the present invention, a method for stimulating tissue having a capacitance, including:

applying a potential to the tissue so as to cause a voltage to develop across the capacitance of the tissue;

injecting a current to the tissue so as to discharge the capacitance;

monitoring the potential to generate a monitored potential; and controlling the current in response to the monitored potential.

The present invention will be more fully understood from the following detailed description of the preferred embodiments thereof, taken together with the drawings, a brief description of which follows.

BRIEF DESCRIPTION OF THE DRAWINGS

FIGS. 2A and 2B are electronic diagrams of a circuit comprised in the device of FIG. 1, according to preferred embodiments of the present invention;

FIGS. 8A and 8B are electronic diagrams of an alternative circuit comprised in the device of FIG. 1, according to preferred embodiments of the present invention;

FIGS. 9 and 10 are voltage vs. time graphs for the circuit of FIGS. 8A and 8B;

FIG. 12 are voltage vs. time graphs illustrating the operation of the flowchart of FIG. 11.

DETAILED DESCRIPTION OF PREFERRED EMBODIMENTS

Figure 1:
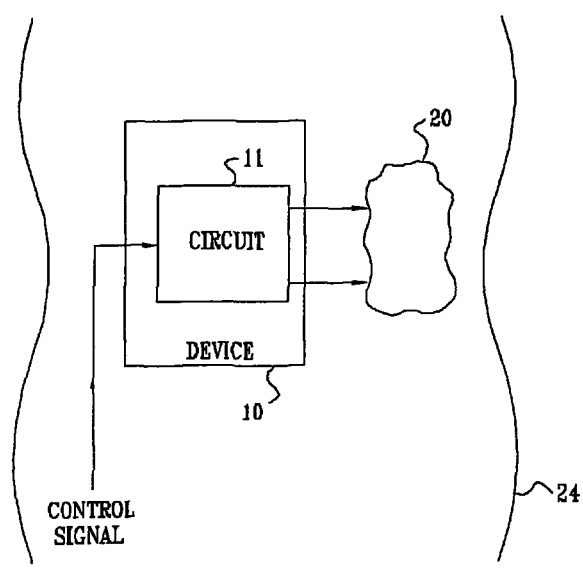
FIG. 1 is a schematic diagram illustrating a stimulation device, according to a preferred embodiment of the present invention.

Reference is now made to FIG. 1, which is a schematic diagram illustrating a stimulation device 10, according to a preferred embodiment of the present invention. Device 10 comprises a circuit 11 which is used to generate electrical waveforms, the waveforms in turn stimulating tissue 20 of a subject 24. Preferably, tissue 20 comprises a muscle, most preferably a sphincter muscle, or a nerve of the subject, although it will be appreciated that tissue 20 may comprise any tissue of subject 24. Device 10 is preferably implanted in the subject, and after implantation and adjustment, is most preferably operated by a control signal generated by subject 24 and input to circuit 11. Circuit 11 may be implemented as discrete components, or as a custom-built component such as an application specific integrated circuit (ASIC), or as a combination of discrete and custom-built components. By way of example, the description hereinbelow applies when circuit 11 comprises discrete components.

An equivalent circuit 21 for tissue 20 comprises an approximately ohmic resistor R2 in series with an interface capacitor having a capacitance $C1(f)$, where f is a frequency of a stimulation applied to the tissue. An approximately ohmic resistor R1 is coupled in parallel with R2 and $C1(f)$. Typical values for R1, R2, and $C1(f)$ are of the order of 1 MΩ, 200Ω, and 40 µF. It will be understood that the values for R1, R2, and $C1(f)$ are dependent on factors such as the type, state, and size of tissue 20. Furthermore, the values of R1, R2, and $C1(f)$ are also typically highly dependent on the shape, size, and type of material of the electrodes used to apply stimulation to tissue 20, as well as on the frequency and voltage of the stimulation applied to the interface capacitor.

Figure 2B:
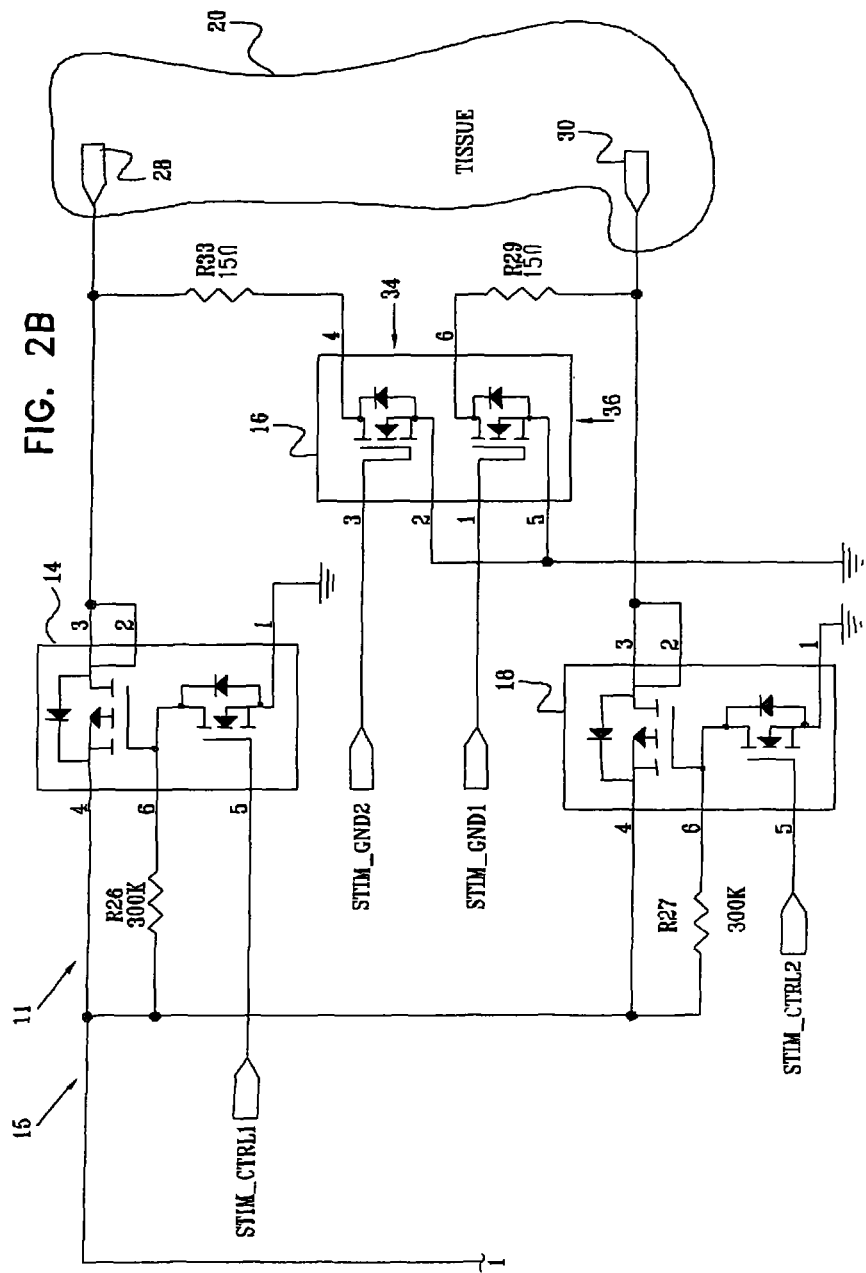

FIGS. 2A and 2B are electronic diagrams of circuit 11, according to preferred embodiments of the present invention. Circuit 11 is powered by a battery 26, which preferably has a maximum voltage approximately equal to 3.2 V. Circuit 11 comprises a charging circuitry section 13 (FIG. 2A) and a switching circuitry section 15 (FIG. 2B). A micro-controller (MC) 22 acts as an overall controller of circuit 11, using as an input the control signal referred to in FIG. 1. Preferably, MC 22 comprises an XE88LC01 produced by Xemics SA of Neuchatel, Switzerland, although any other suitable micro-controller may be used. MC 22 includes, inter alia, a memory 23 wherein parameters for operating circuit 11 may be stored, and an analog-to-digital converter (ADC) 25, which converts analog voltage levels to digital values.

Charging circuitry section 13 operates in two modes, a direct current (DC) mode and an alternating current (AC) mode. The DC mode is activated when a switching device 17 (Q6) is connected so that a positive terminal of battery 26 is coupled to parallel resistors R19 and R20, each resistor most preferably having approximate values of 150Ω. In the DC mode the positive terminal is de-coupled from resistor R21, which most preferably has an approximate value of 15Ω. Values of resistors R19 and R20 are chosen so as to prevent a current from battery 26 exceeding an allowed maximum battery current value. Switch 17 is most preferably implemented from an FDC6306P produced by Fairchild Semiconductor Corporation of South Portland, Me. and the DC mode is activated by micro-controller 22 enabling control signal STIM_EN1 and disabling STIM_EN2.

In the DC mode, a switch 12 (Q8)—most preferably implemented from a field effect transistor (FET) such as an IRLML2402 produced by International Rectifier Corporation of El Segundo, Calif.—is open, so that battery 26 charges capacitors C13 and C15, which both preferably have a value approximately equal to 22 μF, in an RLC circuit formed by resistors R19, R20, an inductor L1, and the capacitors. During operation of circuit 11, the DC mode most preferably operates for a time period, defined by MC 22, no greater than approximately 3·τ seconds, where τ is a charging time constant equal to the RC value of R19, R20, C13, and C15, i.e., $75 \cdot 44 \cdot 10^{-6}$. It will be understood that by charging the capacitors for this length of time (when the capacitors start in a completely discharged state), C15 achieves approximately 95% of the potential of battery 26.

The AC mode is activated when switch 17 couples the positive terminal of battery 26 to R21, while R19 and R20 remain coupled as for the DC mode. MC 22 activates the AC mode by enabling control signals STIM_EN1 and STIM_EN2. In the AC mode switch 12 is rapidly switched closed and open by a rectangular signal STIM_SW, generated by the micro-controller, alternating between on and off states. Most preferably, STIM_SW is on for approximately 4 μs, and off for approximately the same time interval. An alternative timing for STIM_SW is described with reference to FIGS. 8A and 8B below. When switch 12 is closed, inductor L1, preferably having an approximate value of 68 μH, is energized by current through the inductor flowing to ground. When switch 12 is open, current from inductor L1 is diverted via a diode D4 to charge capacitor C15. Assuming that a combined resistance of an internal resistance of inductor L1 and switch 12 is approximately 600 mΩ, approximately 99.7% of the current flowing in the inductor charges capacitor C15. Preferably, a switch 19, most preferably a Reed switch, is positioned before capacitor C15 for use as a safety cut-out.

It will be appreciated that operating circuit 11 in the AC mode as described above enables capacitor C15 to be charged to a high voltage, most preferably of the order of 9 V, which is substantially independent of a voltage supplied from battery 26 and which is only limited by the time during which the AC mode is operative. It will also be appreciated that from an energy efficiency point of view, it is preferable to use the AC mode rather than the DC mode for charging capacitor C15. The charging rates for both modes may be calculated from values of elements of circuit 11, including a potential delivered by battery 26, as will be apparent to those skilled in the art. The rates are preferably stored in memory 23. In some preferred embodiments of the present invention, which mode is used, and for how long the mode is implemented, is a function of a voltage differential to which capacitor C15 is to be charged, respective rates of charging for the DC and AC modes, and a time during which the capacitor is available for charging. A more detailed description of capacitor C15 charging by utilizing stored charging rates is given below.

During operation of circuit 11, micro-controller 22 monitors the voltage across capacitor C15 using resistors R22 and R24 coupled in series across C15, the resistors acting as a voltage divider. The monitored voltage is converted to digital values using ADC 25. Preferably, memory 23 also comprises an ADC look-up table 29, the function and composition of which is described with reference to FIG. 7 below.

In section 15 (FIG. 2B), capacitor C15 is used to generate pulses at a first electrode 28 and a second electrode 30 implanted in tissue 20, via operation of switches 14, 16, and 18. Capacitor C15 thus acts as a stimulation source for the implanted electrodes, and is herein also referred to as a stimulation capacitor. Switches 14 and 18 are implemented as single pole single throw (SPST) switches, preferably integrated load switches FDC6324L produced by Fairchild Semiconductor Corporation, although any other suitable switches may be used. Switch 16 comprises two separate SPST switches 34 and 36, preferably implemented from an integrated load switch FDC6324L, produced by Fairchild Semiconductor Corporation.

Table I below shows states of switches 14, 18, 34, and 36, and respective control signals, as used to generate a positive-going pulse, where electrode 28 is positive with respect to electrode 30, and a negative-going pulse, where electrode 28 is negative with respect to electrode 30.

TABLE I

| Switch | Switch Control | Switch state Positive-going pulse | Switch state Negative-going pulse |
| --- | --- | --- | --- |
| Switch 14 | STIM_CTRL1 + | closed | open |
| Switch 18 | STIM_CTRL2 − | open | closed |
| Switch 36 | STIM_GND1 + | closed | open |
| Switch 34 | STIM_GND2 − | open | closed |

Resistors R29 and R33, each approximately equal to 15Ω, respectively act as current limiting resistors for positive-going and negative-going pulses. Current limitation may typically be required in the event of an inadvertent short between electrode 28 and electrode 30.

MC 22 sets switches 14, 18, 36, and 34 according to Table I, in order to produce pulses as required. MC 22 is also able to monitor an impedance of tissue 20, by measuring the discharge of stimulation capacitor C15 as pulses are generated in tissue 20, as described in more detail below.

Figure 3:
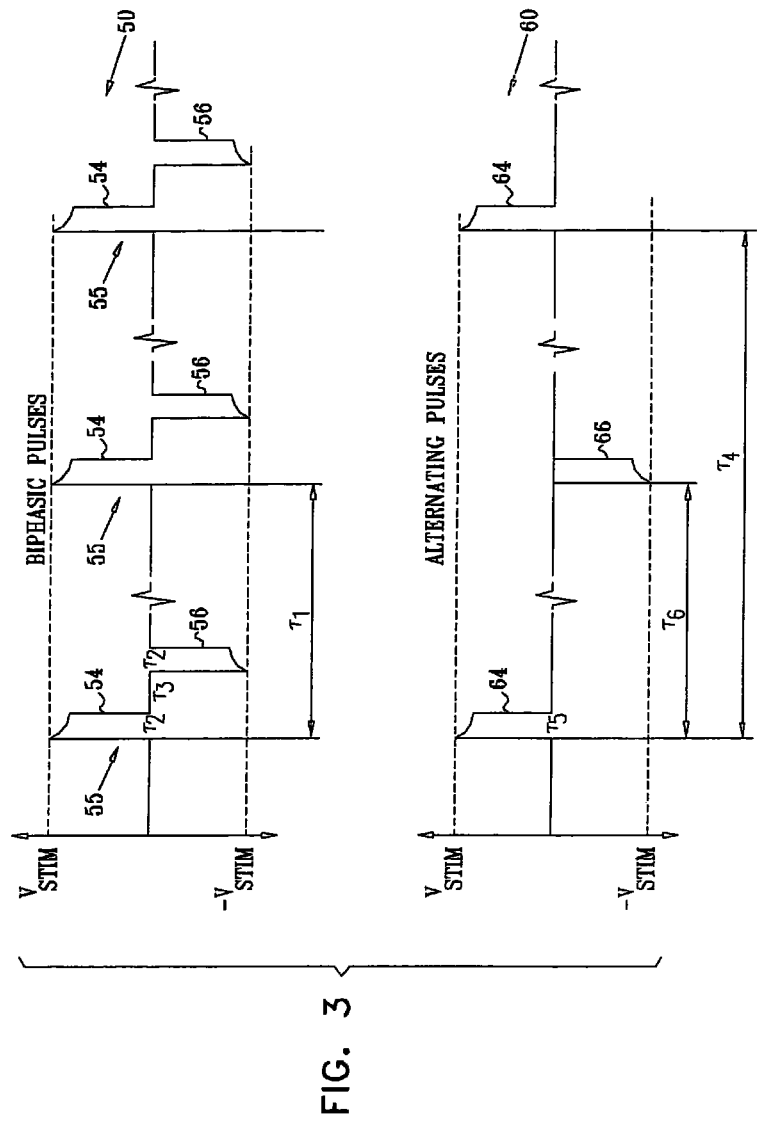
FIG. 3 shows graphs of voltage versus time for different types of pulses generated in the circuit, according to a preferred embodiment of the present invention.

FIG. 3 shows graphs of voltage versus time for different types of pulses generated in circuit 11, according to a preferred embodiment of the present invention. A graph 50 illustrates biphasic pulses 55 generated at electrodes 28 and 30, the biphasic pulses having a period of $\tau_1$. Each biphasic pulse 55 is formed from a uni-directional pulse 54 and a uni-directional pulse 56 which are substantially mirror images of each other, having substantially equal pulse width times $\tau_2$. Pulse 54 is a positive-going pulse having an initial potential $V_{stim}$, pulse 56 is a negative-going pulse having an initial potential $-V_{stim}$. A time $\tau_3$ between pulses 54 and 56 is very much less than the period $\tau_1$ of the pulses.

A graph 60 illustrates alternating pulses 64 and 66 generated at electrodes 28 and 30, having a period of $\tau_4$. Pulses 64 and 66 are substantially mirror images of each other, having substantially equal pulse width times $\tau_5$. Pulse 64 is a uni-directional positive-going pulse having an initial potential $V_{stim}$, pulse 66 is a uni-directional negative-going pulse having an initial potential $-V_{stim}$. However, unlike pulses 54 and 56, a time $\tau_6$ between alternating pulses 64 and 66 is approximately equal to half the period $\tau_4$ of the pulses.

Most preferably, initial values for $V_{stim}$ and times $\tau_1, \tau_2, \tau_3, \tau_4, \tau_5$, and $\tau_6$ are implemented by an operator of device 10, in conjunction with feedback from subject 24, in order to correctly stimulate tissue 20, and the values are stored in memory 23. It will be appreciated that more than one set of initial values of $V_{stim}$ and times $\tau_1, \tau_2, \tau_3, \tau_4, \tau_5$, and $\tau_6$ may be stored, and each particular set of values may be implemented by subject 24 or by the operator. For example, if tissue 20 comprises a sphincter muscle of the urinary tract, a first set of values may have $V_{stim}$ equal to approximately 6V, and times $\tau_1, \tau_2, \tau_3, \tau_4, \tau_5$, and $\tau_6$ equal to approximately 25 ms, 1 μs, 500 μs, 50 ms, 1 μs, and 25 ms respectively. A second set of values may have $V_{stim}$ equal to approximately 2V, and times $\tau_1, \tau_2, \tau_3, \tau_4, \tau_5$, and $\tau_6$ equal to approximately 100 ms, 1 μs, 500 μs, 200 ms, 1 μs, and 100 ms respectively. Micro-controller 22 may use either or both sets, and/or other similar sets of parameters, in order to stimulate tissue 20.

Micro-controller 22 implements both alternating and biphasic pulses by operating switches 17 and/or 12 to charge stimulation capacitor C15 to a voltage $V_{stim}$. Once the capacitor has been charged, switches 14, 16, and 18 are operated, as described with reference to Table I above, to generate the pulses.

Figure 4:
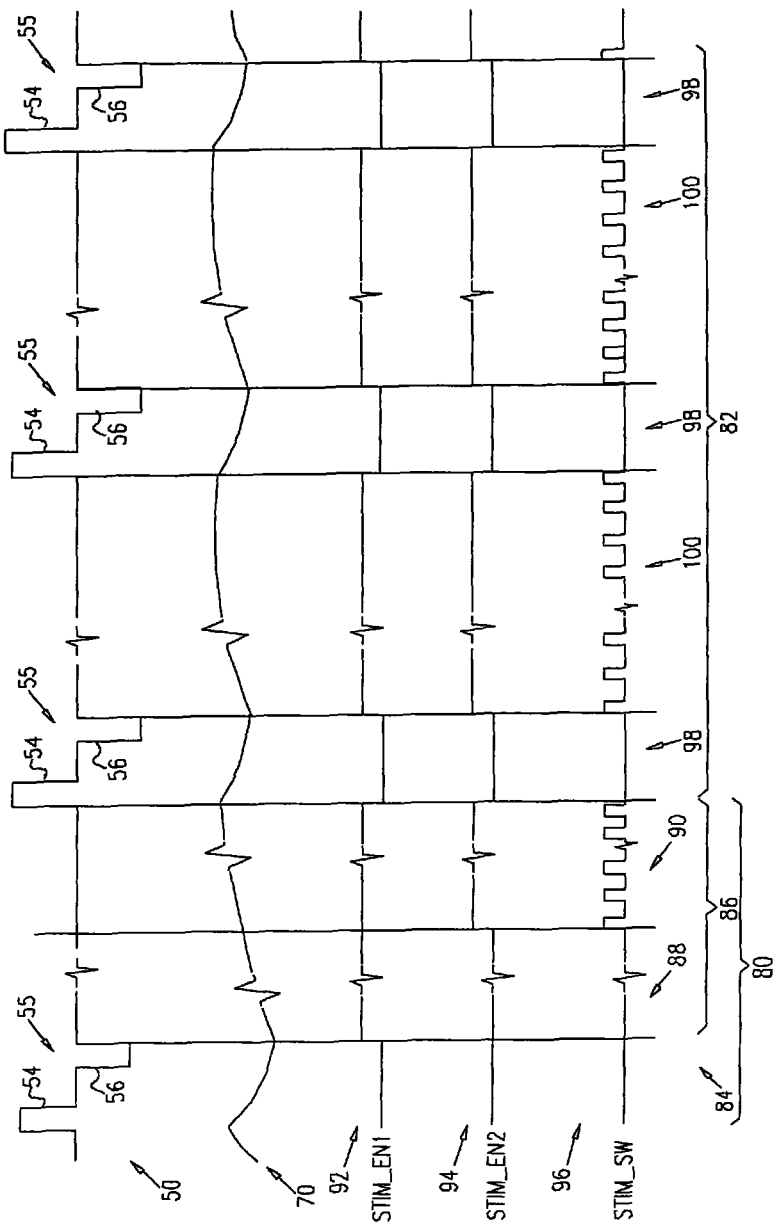
FIG. 4 shows graphs of voltage versus time for elements of the circuit when one of the types of pulses illustrated in FIG. 3 is generated, according to a preferred embodiment of the present invention.

FIG. 4 shows graphs of voltage versus time for elements of circuit 11 when the biphasic pulses illustrated in FIG. 3 are generated, according to a preferred embodiment of the present invention. Generally similar graphs of voltage versus time for the elements apply for generation of alternating pulses. Typically, circuit 11 generates a sequence of pulses (biphasic or alternating) on receipt of the control signal (FIG. 2A) at MC 22. Preferably, if tissue 20 comprises a sphincter muscle, the control signal is derived from a pressure sensor activated by subject 24. Most preferably, a level of the control signal is used to determine which type of pulses (biphasic and/or alternating) are produced by circuit 11.

The graphs of FIG. 4 illustrate voltages versus time for capacitor C15 in a period 80 before the capacitor reaches a quasi-steady state, and in a period 82 when the capacitor is in the quasi-steady state. By way of example, $\tau_1, \tau_2$, and $\tau_3$ for the biphasic pulses of graph 50 are assumed to be approximately 20 ms, 1 μs, and 500 μs respectively, battery 26 is assumed to supply 3V, and the biphasic pulses have a quasi-steady state amplitude of 3.5V, although it will be appreciated that circuit 11 may implement other values for these parameters.

A graph 70 represents the voltage on capacitor C15. At the beginning of a period 84, at which time circuit 11 is required to generate a biphasic pulse, capacitor C15 has been charged to 3V. The biphasic pulse generated in period 84 causes capacitor C15 to discharge at the end of period 84 to 2V.

At the end of period 84, MC 22 preferably evaluates periods during which the DC mode and the AC mode are to be implemented. Preferably, the period for the AC mode is made as large as possible, since charging using the AC mode is more efficient than using the DC mode. The evaluation is based on the charging rates for the DC mode the AC mode (stored in memory 23), a desired voltage differential to be achieved, and an available time for charging. Thus, for a time period 86 following period 84, the desired voltage differential is 1.5V and the available time is approximately 20 ms. By way of example, MC 22 is assumed to set a DC mode period 88 of approximately 8 ms, and an AC mode period 90 of approximately 12 ms.

An alternative method by which MC 22 is able to charge stimulation capacitor C15 is described with reference to FIG. 5 below.

Voltage waveforms for STIM_EN1, STIM_EN2, and STIM_SW are shown in graphs 92, 94, and 96 respectively. Time period 88 is implemented by enabling STIM_EN1. Time period 90 is implemented by enabling STIM_EN1 and STIM_EN2. During period 90, STIM_SW pulses activate switch 12, as described above, and at the end of period 90 capacitor C15 has charged to 3.5V, so that quasi-steady state period 82 begins.

During periods 98, circuit 11 generates biphasic pulses of amplitude 3.5V, and capacitor C15 discharges from 3.5V to 2.5V. At the end of each period 98, MC 22 preferably makes an evaluation, substantially similar to that described above for the end of period 84, for charging periods 100. Herein MC 22 is assumed to set an AC mode period of approximately 20 ms, so that the DC mode is not implemented for periods 100, as is illustrated by graphs 92, 94, and 96. If capacitor C15 charges to the required voltage, STIM_EN1 and STIM_EN2 are disabled, and STIM_SW terminates, as shown in periods 101. Alternatively, MC 22 implements the method of FIG. 5 for charging capacitor C15.

It will be appreciated that by being able to use either or both AC and DC charging modes, circuit 11 is able to reach a quasi-steady state quickly and efficiently, and is also able to maintain the quasi-steady state with a minimal waste of energy. Both factors are important for optimal implementation of battery powered implanted devices delivering sequences of pulses.

Figure 5:
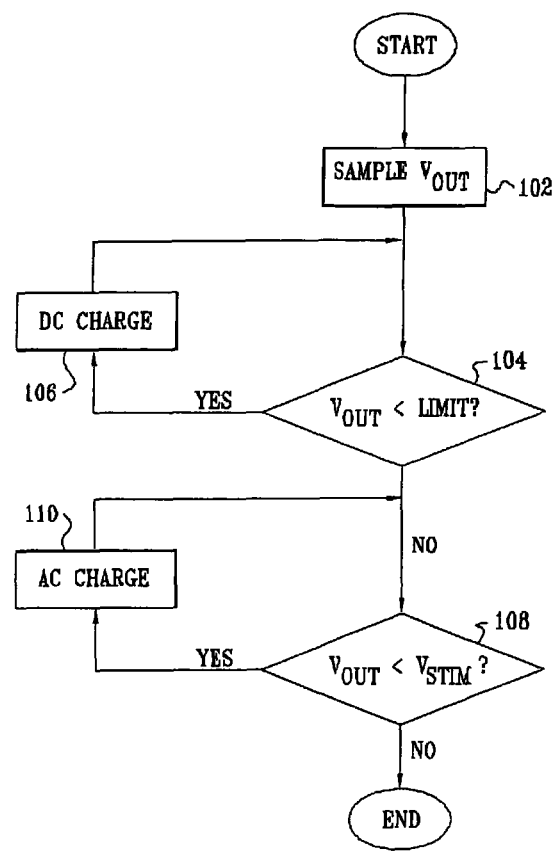
FIG. 5 is a flowchart showing a process for charging a capacitor in the circuit, according to a preferred embodiment of the present invention.

FIG. 5 is a flowchart showing an alternative process 101 for charging capacitor C15, before generating pulses 55, 64, and 66 (FIG. 3), according to a preferred embodiment of the present invention. Process 101 does not rely on knowledge of charging rates of the DC and AC mode of circuit 11.

In an initial step 102 of the process, the voltage $V_{out}$ across C15 is measured by MC 22 sampling the potential at the junction of R22 and R24.

In a first decision step 103, MC 22 compares the value of $V_{out}$ with a required voltage stimulation value $V_{stim}$ stored as described above in memory 23. If $V_{out}$ is greater than or equal to $V_{stim}$, process 101 ends. If $V_{out}$ is less than $V_{stim}$, process 101 continues to a second decision step 104.

In decision step 104, MC 22 compares the value of $V_{out}$ determined in step 102 with a limit value which is set to be a function of a voltage delivered by battery 26. Most preferably, the limit value is implemented to be approximately 90% of the battery voltage, although another value, less than the battery voltage, may be used. If $V_{out}$ is greater than or equal to the limit value, process 101 continues to a third decision step 108. If $V_{out}$ is less than the limit value, in a DC charging step 106 the DC charging phase of section 13 is implemented, by setting STIM_EN_1, and ensuring that STIM_EN_2 is not set. DC charging step 106 is preferably activated for a period of approximately 1 ms, after which step 102 is implemented. The process of cycling through steps 102, 103, 104, and 106 continues for up to five times, or until step 104 is not satisfied.

In third decision step 108, MC 22 compares the value of $V_{out}$ with $V_{stim}$. If $V_{out} < V_{stim}$, then MC 22 initiates an AC charging step 110, during which the AC charging phase of section 13 is implemented, by setting STIM_EN_1 and STIM_EN_2.

During step 110, switch Q8 is toggled between on and off states, as described above. When Q8 is in its off state, MC 22 measures $V_{out}$, as described for step 102. The process of AC charging continues until step 108 is no longer valid, i.e., $V_{out}=V_{stim}$. Alternatively, the AC charging continues until the time at which a pulse is to be generated, corresponding to the end of periods $\tau_1$ or $\tau_6$ (FIG. 3), at which point process 101 terminates.

It will be appreciated that, depending on the differential potential to which capacitor C15 is to be charged, and on the time period available for charging, process 101 may invoke operation of the AC or the DC circuits of section 13, or both circuits.

Returning to FIGS. 2A, 2B, and 3, MC 22 measures a potential on stimulation capacitor C15 at the end of each pulse. MC 22 uses this value, the initial value $V_{stim}$ of the pulse, and the period $\tau_2$ for biphasic pulses (or $\tau_5$ for alternating pulses), to evaluate an impedance of tissue 20, most preferably from an impedance look-up table 27 stored in memory 23. (MC 22 may obtain values of $V_{stim}$, $\tau_2$ and $\tau_5$ from memory 23.) During periods when MC 22 determines that the impedance of tissue 20 is substantially constant, values of $V_{stim}$, $\tau_2$ and $\tau_5$ are not altered In the event that the impedance does alter, MC 22 most preferably alters the value of $V_{stim}$ so that an average current generated by the pulses is substantially constant. Alternatively or additionally, MC 22 alters the width of the pulses so that the average current is substantially constant. Any altered values are stored in memory 23, and are used by MC 22 in subsequent pulse generation. Measurements of the impedance, as described above, enable MC 22 to detect open or short circuits, such as may occur by misplacement of one of electrodes 28, 30.

It will be appreciated that both biphasic and alternating pulses generated by preferred embodiments of the present invention comprise sequential pulses which are substantially equal in magnitude but opposite in direction to each other. Thus, charge transfer when the pulses are applied to tissue 20 is substantially equal in magnitude but opposite in direction. Thus, substantially no electrolysis occurs during stimulation to the tissue, because interface capacitance C1(f) is discharged by the opposite sign pulses comprised in the biphasic or alternating pulses. This is in contrast to prior art systems applying mono-phase pulses to tissue 20, in which cases capacitance C1(f) slowly discharges through resistors R1 and R2, effectively causing electrolysis of tissue 20.

It will also be appreciated that by measuring the impedance of tissue 20 as described above, and by adjusting stimulation parameters responsive to the impedance, there is no need for measuring or estimating current in tissue 20 by a separate current-sensing circuit, as is implemented in systems known in the art for stimulating tissue.

The biphasic pulses described hereinabove, and illustrated in graph 50 (FIG. 3 and FIG. 4), each comprise a positive-going pulse followed by a negative-going pulse. Such a non-alternating sequence of biphasic pulses may be represented as (+−), (+−), (+−), (+−), . . . . It will be appreciated that the biphasic pulses may each comprise a negative-going pulse followed by a positive-going pulse, which non-alternating sequence may be represented as (−+),(−+),(−+),(−+), . . . . It will be further appreciated that the biphasic pulses may be alternated in a regular or an irregular sequence, so that alternating sequences of biphasic pulses of the form (+−), (−+), (+−), (−+),(+−), . . . , or (+−), (+−), (−+), (+−),(+−), . . . , or of any other regular or irregular sequence may be generated. The application of alternating sequences of biphasic pulses may reduce electrolysis effects at electrodes 28 and 30 (FIG. 2B). All forms and combinations of non-alternating and alternating sequences of biphasic pulses are assumed to be comprised within the scope of the present invention.

Figure 6:
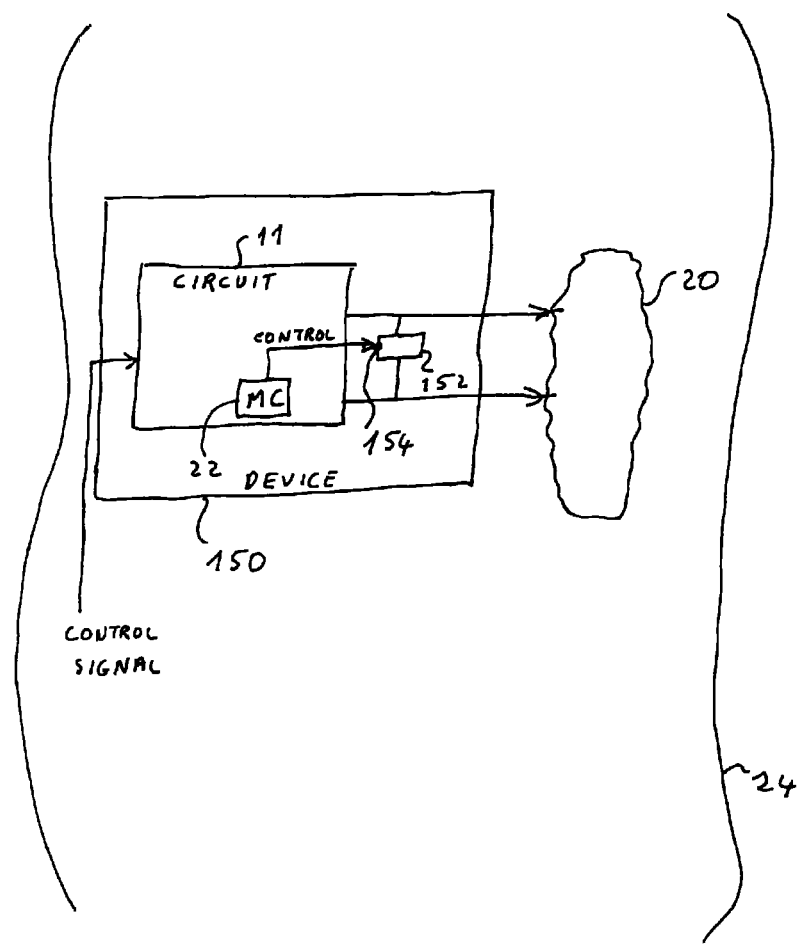
FIG. 6 is a schematic diagram illustrating an alternate stimulation device, according to a preferred embodiment of the present invention.

FIG. 6 is a schematic diagram illustrating an alternate stimulation device 150, according to a preferred embodiment of the present invention. Apart from the differences described below, the operation of device 150 is generally similar to that of device 10 (FIGS. 1, 2A, 2B, and 3), so that elements indicated by the same reference numerals in both devices 150 and 10 are generally identical in construction and in operation. Device 150 comprises a controllable element 152 which is connected between electrodes 28 and 30, and which is able to act as an effective short-circuit therebetween, responsive to a control signal from MC 22. Element 152 preferably comprises a resistor in series with an FET such as an IRLML2402, or alternatively any other set of electronic components, such as will be apparent to those skilled in the art, which are able to act as a controllable short-circuit The resistance of element 152, when it is operating as a short-circuit, is preferably significantly less than R1, typically having a value of the order of hundreds of ohms. Most preferably, the resistance of element 152 is set by MC 22 so that no anodal break excitation occurs in tissue 20.

The control signal for element 152 is input to a control electrode 154 of the element, the control electrode comprising a gate of an FET if element 152 is implemented therefrom. Most preferably, MC 22 activates the control signal directly after a biphasic pulse or an alternating pulse has been impressed on electrodes 28 and 30. By activating the control signal directly after the pulses, and thus short-circuiting the electrodes, the level of stimulation to tissue 20 is more effectively controlled. Furthermore, any residual charge on the electrodes from the pulses charging interface capacitance C1(f) is substantially neutralized, so reducing electrolysis caused by discharge of the capacitance.

Figure 7:
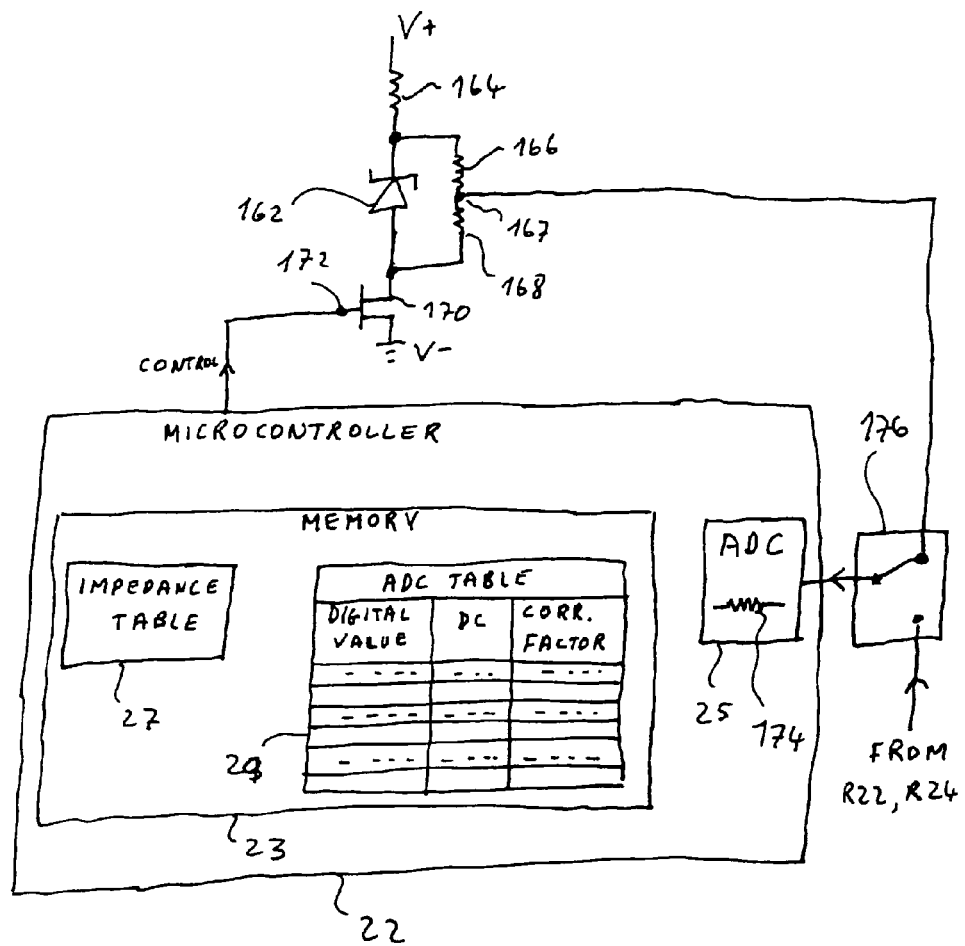
FIG. 7 is a schematic electronic diagram of a calibration circuit, according to a preferred embodiment of the present invention.

FIG. 7 is a schematic electronic diagram of a calibration circuit 160, according to a preferred embodiment of the present invention. Circuit 160 is most preferably included in device 10 and device 150, and is used as a reference for correcting inaccuracies in the operation of ADC 25. Apart from the differences described below when circuit 160 is implemented, operations of devices 10 and 150 are generally as described above with reference to FIGS. 1, 2A, 2B, 3 and 6.

Implanted devices such as device 10 and device 150 are expected to operate for a number of years before battery recharging, or before device or battery replacement. The device thus needs to operate over relatively large variations of battery voltage. However, the output of analog-to-digital converters such as ADC 25 is not invariant with battery voltage (applied to MC 22 wherein ADC 25 is located) and so a method of correction of any such variation is highly desirable.

Circuit 160 comprises a resistor 164, a zener diode 162, and an FET 170 acting as a switch. The resistor, zener diode, and switch are connected as a series circuit between V+ and V− (FIG. 1). A gate electrode 172 is coupled to a control port of MC 22. Thus, MC 22 may effectively toggle the series circuit on or off, by application of a control voltage to electrode 172. When the series circuit is on, the circuit acts as a voltage regulator supplying a substantially invariant voltage, even with variation of voltage from battery 26, at a junction 169 between the zener diode and resistor 164. Other circuits or electronic devices driven by battery 26, for producing a substantially invariant voltage, will be apparent to those skilled in the art. All such circuits and electronic devices are assumed to be comprised within the scope of the present invention.

A pair of resistors 166 and 168 are connected in series and shunt zener diode 162, the resistor pair acting as a voltage divider having an output at a junction 167 of the resistor pair. Preferable values for resistors 164, 166, and 168 are approximately 1.5 kΩ, and zener diode 162 preferably has an operating voltage of approximately 1.2 V and a "striking" current of approximately 1 mA. Thus, battery voltages greater than about 2.2 V cause zener diode 162 to strike, and generate a substantially invariant voltage of 0.6 V at junction 167. Typically, battery 26 is considered depleted if the battery voltage is lower than about 2.2 V.

The output from junction 167 is fed by an SPDT switch 176 to ADC 25. Switch 176 is controlled by MC 22, and in a first position the switch couples junction 167 to ADC 25. In a second position the switch couples the junction of R22 and R24 to the ADC, as described above with reference to FIG. 2A.

Before operation of device 10 or device 150, ADC look-up table 29 is stored in memory 23. The table comprises outputs of ADC 25 when input with the voltage from junction 167, respective voltages of battery 26, and respective multiplicative correction factors to be applied to the outputs of the ADC. (It will be understood that when battery 26 is operating at its nominal voltage, the output of ADC 25 will be substantially correct, and the correction factor in this case is 1.) Most preferably, the table allows for changes in actual value of voltage input to the ADC due to an internal resistance 174 of the ADC, the internal resistance typically being a value of approximately 150 kΩ.

To calibrate ADC 25 during operation of device 10 or 150, the micro-controller sets switch 176 to be in its first position, and sets FET 170 to conduct so that the voltage of junction 167 is input to the ADC. An output from ADC 25 is recorded by MC 22, and the micro-controller uses table 29 to determine the battery voltage, and to determine the correction factor to be applied to readings derived from ADC 25 due to a change of battery voltage from its nominal value. Most preferably, the battery voltage and the correction factor are determined using linear interpolation of values present in table 29, or by any other method known in the art. As changes in battery voltage occur, MC 22 uses the new values of battery voltage and the correction factor for ADC 25 to ensure that the average current generated by the pulses, described above with reference to FIGS. 4 and 5, is substantially constant.

The calibration described hereinabove may be implemented at any convenient time, as determined by MC 22, most preferably when there is no requirement for device 10 or device 150 to generate stimulation pulses. Because of the generally slow rate of change of battery voltage with time, such calibrations will normally only need to be implemented relatively infrequently, such as at 24 hourly intervals. Such a regular calibration time is preferably programmed into MC 22 at installation of device 10 or 150. Most preferably, MC 22 monitors changes in battery voltage as determined by the calibration, and is adapted to change the times of calibration in the event of any relatively sudden change in battery voltage, such as a relatively sharp voltage decrease. It will be appreciated that the calibration system described hereinabove allows for measuring the voltage output from battery 26, as well as correcting for inaccuracies in ADC 25 output due to changes in the battery output voltage from a nominal output value. Measurements of the voltage output of battery 26 enable determinations of the remaining lifetime of the battery, as well as providing an indication of when the battery is near the end of its life.

Figure 8B:
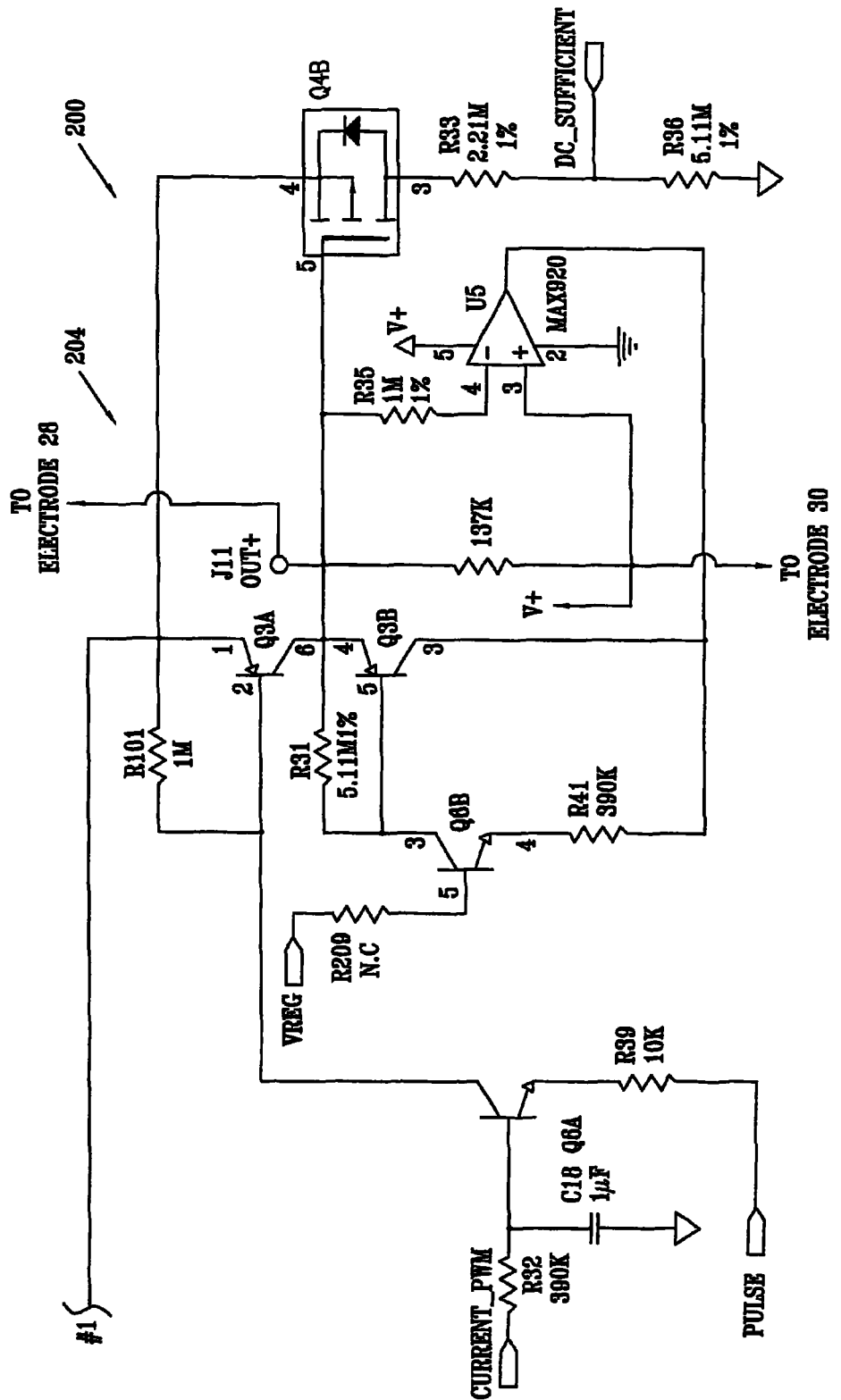

FIGS. 8A and 8B are electronic diagrams of an alternative circuit 200 comprised in device 10 (FIG. 1), according to preferred embodiments of the present invention. Circuit 200 comprises a charging circuitry section 202, (FIG. 8A) and a current controlled stimulation section 204 (FIG. 8B). Apart from the differences described below, charging circuitry section 202 is generally similar to that of the AC elements of charging circuitry section 13 (FIG. 2A), such that elements indicated by the same reference numerals in both sections 13 and 202 are generally identical in construction and in operation. Elements R21, C13, C14, L1, C16, R22, and R24 in section 13 correspond respectively to R42, C19, C20, L2, R43, and R45 in section 202. A pair of capacitors C21 and C22 act as stimulation capacitors, corresponding to stimulation capacitor C15 (FIG. 2A). In contrast to capacitor C15 which is connected to ground, a first side of stimulation capacitors C21 and C22 is connected to the positive supply of battery 26, so that components in section 204 have sufficient operating voltage.

Section 202 charges stimulation capacitors C21 and C22 generally as described for the AC mode operation of section 13. However, rather than pulses STIM_SW having approximately equal on and off times, MC 22 is configured to vary the off time according to a look-up table 206 in memory 23. Table 206 comprises values of VCAP_DIV, i.e., the voltage measured by the resistance divider formed by R43 and R45, and corresponding to the charged voltage VCAP of capacitors C21 and C22. Table 206 gives "off" times for STIM_SW for different values of VCAP_DIV. MC 22 receives VCAP_DIV as an input, and uses the table to find the off time for STIM_SW.

Values for table 206 are most preferably determined experimentally, or alternatively by simulation of circuit 200, prior to installation of device 10 in subject 24. Typical off times are in a range from approximately 20 μs to approximately 50 μs to generate voltages up to approximately 25 V. By implementing variable off times for STIM_SW, the inventors have found that charge times for stimulation capacitors C21 and C22 are substantially reduced compared to having the off time fixed. It will be appreciated that reduced charge times for the stimulation capacitors means that operations of MC 22 may be substantially reduced during times when the capacitors are not being charged, leading to further overall improvements in efficiency of device 10.

In section 204 (FIG. 8B) complementary npn transistors Q6A, Q6B, and pnp transistors Q3A, Q3B, typically BC847 and BC857 transistors produced by Philips Semiconductors of Eindhoven, The Netherlands, are used to develop stimulation levels for electrodes 28 and 30. Section 204 receives VCAP at the emitter of Q3A. MC 22 generates pulse width modulated pulses CURRENT_PWM, having a variable duty cycle. The CURRENT_PWM pulses are filtered in a low pass filter comprised of R32 and C18, generating a substantially constant voltage which is input to the base of Q6A. The higher the duty cycle of CURRENT_PWM, the higher the voltage input to Q6A, and thus the higher the current through Q6A, providing a level PULSE is set to ground. If PULSE is set high, current through Q6A effectively reduces to zero. Thus, PULSE acts as a switching level for section 204, and CURRENT_PWM acts to set the current level of the section when the section is supplying current.

The current from Q6A is input to the base of Q3A, which multiplies the base current, so that Q6A and Q3A together act as a current source. The current source is activated by setting PULSE to ground, whereupon stimulation current is injected into tissue 20 via J11 through electrode 28. The stimulation current returns through electrode 30 via J9.

When Q3A is active, i. e., is conveying stimulation current through J11, $V_{CE}$, the potential between the emitter and collector of Q3A, has a pre-determined value. A transistor Q4B, preferably a field effect transistor (FET) Sil539 produced by Vishay Siliconix, acts as a detector to monitor $V_{CE}$. Q4B preferably has its source coupled to the emitter of Q3A, and its gate to the collector of Q3A. The drain of Q4B is coupled, via a voltage divider formed by R33 and R36, to ground. If $V_{CE}$ is higher than a threshold voltage of Q4B, then Q4B conducts and a signal DC_SUFFICIENT, from the voltage divider formed by R33 and R36, is generated. MC 22 uses DC_SUFFICIENT to monitor and set the voltage VCAP developed by section 202, as described in more detail below with respect to FIG. 11.

A discharge phase of section 204 is activated when PULSE is set high. During this phase discharge is implemented by setting VREG, into the base of transistor Q6B, high. Typically, VREG is connected to V+. Alternatively, VREG may be connected to the filtered value of CURRENT_PWM. Q6B then passes a current having a value dependent on R41, and on the potential developed by the filtered value of CURRENT_PWM if VREG is connected thereto. The current passed by Q6B is injected to the base of Q3B where it is multiplied to form a discharge current between electrodes 28 and 30. The discharge current, opposite in direction to the stimulation current, effectively discharges interface capacitance C1($f$) of tissue 20. The value of R41 is most preferably set so that the discharge current is significantly less than the charge current, typically by a factor approximately equal to ten or twenty. R41 in section 204 is, by way of example, 390 kΩ. However, R41 may be set to any other suitable fixed value, or may be implemented as an adjustable resistor, or as a resistor having a value that may be programmed by MC 22. The discharge provided by section 204 is an "active" discharge mechanism which is substantially independent of any charge on C1($f$), or of the voltage between electrodes 28 and 30. Advantages of this active discharge are described in more detail below.

Discharge continues until the output of a comparator U5, preferably a MAX920 produced by Maxim Integrated Products, Inc., of Sunnyvale, Calif., goes high. U5 is configured so that its output remains low while there is a substantially non-zero potential at its input, i.e., while there is a substantially non-zero potential across capacitance C1($f$), and so that its output goes high when the potential across the capacitor is substantially equal to zero. It will be appreciated that U5 comprises a feedback loop that governs the discharge of capacitance C1($f$).

FIGS. 9 and 10 are voltage vs. time graphs illustrating operation of circuit 200. A graph 250 shows the voltage between electrodes 28 and 30, and graphs 252 and 254 respectively show voltages of PULSE and the output of U5. In a period 256, PULSE is set high, so that there is no charge current to electrodes 28 and 30, and thus the potential between the electrodes is zero. At a time T1, MC 22 sets PULSE to be low and initiates pulses CURRENT_PWM, causing charge to flow between the electrodes at a rate set by the duty cycle of CURRENT_PWM. The voltage between the electrodes thus rises to an initial value VA, typically approximately 4 V, and the output of U5 consequently goes low. During a period 258, also herein termed $\Delta t_1$ and typically having a value of approximately 1 ms, PULSE remains low, so that charge continues to flow between electrodes 28 and 30 and the voltage between the electrodes rises further, in a substantially linear manner, to a value VB, typically approximately 4.2 V. It will be appreciated that the slope of the graph in period 258 is directly proportional to the stimulation capacitance formed by C21 and C22, and to the stimulation current generated by Q3A.

At a time T2 MC 22 sets PULSE high, so that charge no longer flows to the electrodes, and so that the voltage across the electrodes falls to a value VC, typically approximately 0.2 V. This non-zero voltage maintains the output of U5 low, so that discharge of C1($f$) occurs via Q3B. The discharge lowers the voltage across the electrodes during a period 260, also herein termed $\Delta t_2$ and typically having a value of approximately 10 ms, in a substantially linear manner. The discharge continues until the voltage across the electrodes, detected by U5, is zero, at a time T3. At time T3 the output of U5 thus goes high, cutting off further discharge of C1($f$).

It will be appreciated that the slope of the graph in period 260, generated by the active discharge mechanism described hereinabove, is directly proportional to the stimulation capacitance and to the discharge current generated by Q3B, so that the discharge current is a substantially fixed fraction of the stimulation current. Also, the active discharge mechanism ensures that C1($f$) is substantially completely discharged, regardless of the dependence of R1, R2, and C1($f$) on parameters described above with reference to FIG. 1, by effectively monitoring the charge on the interface capacitance during discharge. The active discharge mechanism provides a substantially linear voltage-time discharge of the interface capacitance, in contrast to "passive" discharge systems which use a resistance, and which exponentially reduce their rate of discharge as the charge on the capacitance reduces.

Furthermore, the inventors have found that application of the active discharge mechanism, as exemplified above, to actively limit the discharge current to a maximum value, typically approximately 5% of the stimulation current, substantially eliminates anodal break excitation.

C1($f$) may be calculated from the measured value of $\Delta t_2$. During discharge of C1($f$), i.e., in period 260, the total charge Q delivered to the interface capacitor is given by:

$$Q = C1(f) \cdot V_S \qquad (1)$$

where $V_S$ is the voltage on the interface capacitor during discharge.

Also, $$Q = I \cdot \Delta t_2 \qquad (2)$$

where I is the discharge current to the interface capacitor from Q3B.

Combining equations (1) and (2) gives:

$$C1(f) = \frac{V_S}{I \cdot \Delta t_2} \qquad (3)$$

Inspection of equation (3) shows that the interface capacitance C1($f$) is inversely proportional to $\Delta t_2$, i.e., the time of discharge, and that C1($f$) may be calculated from the values of $\Delta t_2$, I, and $V_S$. A method for determining $V_S$ is described with reference to equation (4) below.

As stated above, the value of interface capacitance C1($f$) is a function of frequency f applied to tissue 20. Since f is inversely proportional to pulse width $\Delta t_1$, the value of C1($f$) varies as $\Delta t_1$ varies. Thus, by charging the interface capacitor for different times $\Delta t_1$, and measuring the discharge time of $\Delta t_2$ in each case, the value of C1($f$) for different frequencies f may be determined.

Use of equation (3), and the measurement of the variation of the interface capacitance as described above, allow for measurement of the impedance of the interface formed by electrodes 28 and 30 with tissue 20 by methods which will be apparent to those skilled in the art. Measurement of the impedance enables detection of electrode open and short circuits, for example, in cases where the electrode ruptures or moves to a new location. Such open and short circuits typically cause relatively rapid changes of impedance with time, and MC 22 may be implemented to detect the changes and alter or halt the stimulation applied by the electrodes in response to the detected changes.

Knowledge of the values of C1(f) also allows settings to be made for the charge and discharge currents that improve the overall efficiency of operation of circuit 200.

A graph 280 (FIG. 10) shows the voltage between electrodes 28 and 30, and graphs 282 and 284 respectively show voltages of PULSE and the output of U5 for an alternative type of stimulation that may be provided by circuit 200. A time period 286 corresponds to periods 256, 258 and the first part of 260 (FIG. 9). In periods 288 and 290, however, MC 22 sets PULSE to be low and operates pulses CURRENT_PWM, implementing the charging cycle before the voltage across electrodes 28 and 30 has reduced to zero. In a period 292, discharge is allowed between the electrodes, substantially as described above for period 260, until at a time T4 the voltage across the electrodes becomes zero, whereupon the output of U5 goes high. Typically a time between periods 288 and 290 is approximately 5 ms, and period 292 is approximately 20 ms.

It will be appreciated that stimulation pulses other than those exemplified by FIG. 9 and FIG. 10 may be generated by circuit 200, using alternative times for PULSE to be high and low. All such stimulation pulses are assumed to be comprised within the scope of the present invention.

In operating circuit 200, high efficiency is achieved by maintaining stimulation capacitors C21 and C22 at a minimum potential sufficient to drive section 204. Preferred embodiments of the present invention use DC_SUFFICIENT to regulate the potential of the stimulation capacitors so as to achieve such high efficiency, as is described with reference to FIG. 11 below.

Figure 11:
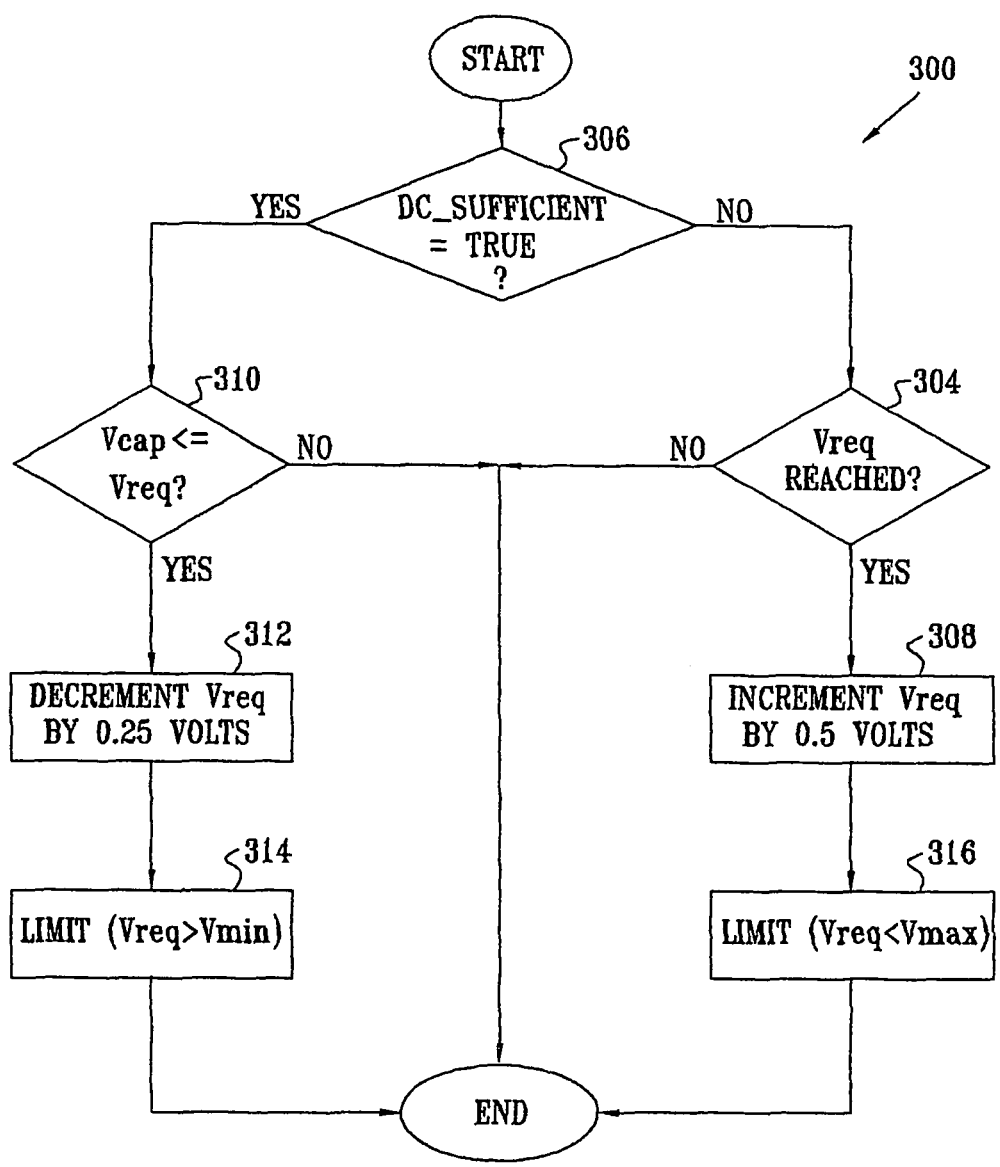
FIG. 11 is a flowchart showing steps involved in setting a voltage in the circuit of FIGS. 8A and 8B, according to a preferred embodiment of the present invention.

FIG. 11 is a flowchart 300 showing steps involved in setting the voltage on stimulation capacitors C21 and C22, according to a preferred embodiment of the present invention. Implementing the steps of the flowchart allows circuit 200 to attempt to minimize an absolute difference between the actual voltage VCAP on the stimulation capacitor and a targeted voltage $V_{REQ}$ for the capacitor, set by MC 22. In following the flowchart, both $V_{REQ}$ and VCAP may vary so as to attempt to minimize the difference.

Referring back to circuit 200, the following condition holds:

$$VCAP = V_{CE} + V_S \quad (4)$$

where $V_S$ is the stimulation potential applied between electrodes 28 and 30, and $V_{CE}$ is the potential between the emitter and collector of transistor Q3A.

It will be appreciated that $V_S$ may be determined from values of VCAP and $V_{CE}$.

During operation of circuit 200, $V_S$ must be sufficient to provide current through tissue 20, and the current is controlled by transistor Q3A. In order to act as a controller, Q3A must be in a conducting state, so that MC 22 must ensure that $V_{CE}$ must be greater than a minimum transistor operating voltage, typically approximately 0.2 V. In addition, MC 22 adjusts $V_{CE}$ to accommodate changes in VCAP, so as to maintain $V_{STIM}$ at the required potential. The state of Q3A is monitored by transistor Q4B, which generates DC_SUFFICIENT. DC_SUFFICIENT acts as a Boolean signal indicating whether Q3A is conducting or not. Preferably, DC_SUFFICIENT is set to be TRUE or FALSE according to the following condition:

$$V_{CE} \geqq V_{OP}, \text{DC\_SUFFICIENT is TRUE},$$

$$V_{CE} < V_{OP}, \text{DC\_SUFFICIENT is FALSE} \quad (5)$$

where $V_{OP}$ is an operating potential at which Q3A is maintained.

Typically, MC 22 sets $V_{OP}$ to be approximately 1.5 V. In the description below, $V_{OP}$ is assumed to be 1.5 V.

MC 22 preferably implements the steps of flowchart 300 at the end of each charging period when PULSE goes high, e.g., at T2 (FIG. 9) and at the end of periods 288 and 290 (FIG. 10).

In a first comparison 306, MC 22 checks the value of DC_SUFFICIENT. If DC_SUFFICIENT is FALSE, then in a second comparison 304 MC 22 checks that $V_{REQ}$ was reached during the charging period. If $V_{REQ}$ was not reached during the charging period the flowchart ends. If $V_{REQ}$ was reached, then in a step 308 $V_{REQ}$ is incremented, typically by a value approximately equal to 0.5V. In a step 316 the value of $V_{REQ}$ is checked to ensure it is less than a limiting operational maximum voltage $V_{max}$. The process of incrementing $V_{REQ}$ thus applies when VCAP<$V_S$+1.5 V.

If comparison 306 returns DC_SUFFICIENT as TRUE, then VCAP>$V_S$+1.5 V. When DC_SUFFICIENT is TRUE, in a third comparison 310 MC 22 compares the value of VCAP with $V_{REQ}$, using the output VCAP_DIV. If VCAP>$V_{REQ}$, then the flowchart ends. If VCAP$\leqq V_{REQ}$, then in a step 312 MC 22 decreases $V_{REQ}$, typically by approximately 0.25V. In a step 314 the value of $V_{REQ}$, is checked to ensure it is greater then a limiting operationla minimum voltage $V_{min}$.

It will be appreciated that implementation of flowchart 300 leads to a system wherein MC 22 varies VCAP by varying $V_{CE}$ about $V_{OP}$. By implementing flowchart 300, MC 22 maintains the stimulation capacitors at a potential that is only slightly greater than the minimum voltage necessary for circuit 200 to operate, leading to very efficient operation of the circuit.

FIG. 12 shows graphs illustrating the operation of flowchart 300, according to a preferred embodiment of the present invention. The graphs are simulations of voltages vs. time when circuit 200 has reached a steady state, assuming a value of $V_{OP}$=1.5 V and a value of $V_S$=4 V. A graph 354 shows values of $V_{REQ}$ set by MC 22; a graph 356 shows values of VCAP on the stimulation capacitor; and a graph 358 shows values of signal DC_SUFFICIENT, a value of 5V corresponding to TRUE, and 4V corresponding to false.

MC 22 operates flowchart at times 352 and 360, corresponding to times just after stimulation has been applied, as shown by the sharp drop in values of VCAP. At a first time 352 (150 ms), DC_SUFFICIENT is TRUE and VCAP<$V_{REQ}$, so that step 312 of flowchart 300 is reached, and MC 22 decrements $V_{REQ}$. The same conditions hold at other times 352, so that in each case $V_{REQ}$ is decremented.

At a first time 360 (550 ms) DC_SUFFICIENT is FALSE and $V_{REQ}$ was reached during the charging period, as shown by VCAP being greater than VREQ in the immediately preceding pulse. Step 308 of flowchart 300 is thus reached, so that MC 22 increments $V_{REQ}$. The same conditions hold at other times 360, in each case $V_{REQ}$ being incremented.

As illustrated by graph 356, operation of flowchart 300 causes VCAP to vary about a value approximately equal to 5.5 V ($V_{OP}$+$V_S$), by effectively incorporating a feedback effect between VCAP and $V_{REQ}$. The feedback effect enables future values of VCAP to correspond with values of $V_{REQ}$. As also illustrated by the graphs, operation of flowchart 300 causes VCAP to always be sufficient for MC 22 to generate stimulation, but never to rise above a maximum value, approximately equal to 6.3 V in the simulation shown.

It will be appreciated that the preferred embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. Apparatus for stimulating tissue having a capacitance, comprising:
   charge circuitry which is adapted to apply a stimulation current to the tissue, causing a voltage to develop across the capacitance of the tissue; and
   discharge circuitry which is adapted to inject a discharge current to the tissue so as to discharge the capacitance, such that, while the discharge current is being injected into the tissue, a value of the discharge current is substantially independent of the voltage across the capacitance,
   the discharge circuitry being adapted to measure the voltage across the capacitance, and to halt injection of the discharge current to the tissue when the voltage is substantially zero.

2. Apparatus according to claim 1, wherein the charge circuitry comprises a stimulation capacitor, an inductor, and a micro-controller which is adapted to apply pulses having a variable duty cycle to the inductor, and wherein the micro-controller causes the inductor to charge the stimulation capacitor to the voltage by altering the variable duty cycle.

3. Apparatus according to claim 1, wherein the discharge circuitry is adapted to inject the discharge current to the tissue, by injecting into the tissue a discharge current that is substantially fixed.

4. Apparatus according to claim 1, comprising a micro-controller which is adapted to measure a time to discharge the capacitance, and to generate a measure of the capacitance in response to the time.

5. Apparatus according to claim 1, comprising a micro-controller which is adapted to measure a time to apply the stimulation current to the tissue, and to generate a measure of the capacitance in response to the time.

6. Apparatus according to claim 1, wherein the discharge circuitry is adapted to inject the discharge current, the discharge current having a value that substantially eliminates anodal break excitation of the tissue.

7. Apparatus according to claim 1, and comprising:
   a battery having a first battery terminal and a second battery terminal coupled to ground and generating a battery voltage which powers at least a first part of the charge circuitry and at least a second part of the discharge circuitry; and
   a first and a second stimulation electrode between which the capacitance is formed,
   wherein the first battery terminal and the first stimulation electrode are connected, and
   wherein the charge circuitry causes the voltage to develop between the first and the second stimulation electrodes, and
   wherein the discharge circuitry injects the discharge current between the first and the second stimulation electrodes.

8. Apparatus according to claim 7, and comprising:
   a stimulation capacitor which receives a stimulation voltage generated by the charge circuitry; and
   a detector which monitors a second-stimulation-electrode potential on the second stimulation electrode,
   the detector being coupled between ground and the stimulation potential.

9. Apparatus according to claim 8, and comprising a micro-controller which receives a Boolean signal from the detector in response to the second-stimulation-electrode potential, and which modifies a targeted voltage for the voltage across the stimulation capacitor, in response thereto.

10. A method for stimulating tissue having a capacitance, comprising:
    applying a stimulation current to the tissue so as to cause a voltage to develop across the capacitance of the tissue;
    injecting a discharge current to the tissue so as to discharge the capacitance, such that, while the discharge current is being injected into the tissue, a value of the discharge current is substantially independent of the voltage across the capacitance;
    measuring the voltage across the capacitance; and
    halting injection of the discharge current to the tissue when the voltage is substantially zero.

11. A method according to claim 10, wherein injecting the discharge current comprises injecting a discharge current that is substantially fixed.

12. A method according to claim 10, and comprising measuring a time to discharge the capacitance, and generating a measure of the capacitance in response to the time.

13. A method according to claim 10, and comprising measuring a time to apply the stimulation current to the tissue, and generating a measure of the capacitance in response to the time.

14. A method according to claim 10, wherein injecting the discharge current comprises injecting the discharge current, the value of the discharge current substantially eliminating anodal break excitation of the tissue.

15. A method according to claim 10, and comprising:
    providing a battery having a first battery terminal and a second battery terminal coupled to ground;
    providing a first and a second stimulation electrode between which the capacitance is formed;
    connecting the first battery terminal and the first stimulation electrode;
    causing the voltage to develop between the first and the second stimulation electrodes;
    injecting the discharge current between the first and the second stimulation electrodes;
    providing a stimulation capacitor which receives a stimulation voltage in response to applying the stimulation current;
    coupling a detector between ground and the stimulation potential; and
    monitoring with the detector a second-stimulation-electrode potential on the second stimulation electrode.

16. A method according to claim 15, and comprising:
    receiving a Boolean signal from the detector in response to the second-stimulation-electrode potential;
    setting a targeted voltage for the voltage across the stimulation capacitor; and
    modifying the targeted voltage in response to the signal.

* * * * *

UNITED STATES PATENT AND TRADEMARK OFFICE
CERTIFICATE OF CORRECTION

PATENT NO. : 8,423,132 B2
APPLICATION NO. : 10/538521
DATED : April 16, 2013
INVENTOR(S) : Vaingast et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2289 days.

Signed and Sealed this
Eighth Day of September, 2015

Michelle K. Lee
*Director of the United States Patent and Trademark Office*